United States Patent
Inoue et al.

(10) Patent No.: US 9,382,303 B2
(45) Date of Patent: *Jul. 5, 2016

(54) VACCINE FOR TREATMENT OF TAUTOPATHY

(71) Applicants: Kyoto University, Kyoto-shi, Kyoto (JP); National Institute of Radiological Sciences, Chiba-shi, Chiba (JP)

(72) Inventors: Haruhisa Inoue, Kyoto (JP); Hiroki Takeuchi, Kyoto (JP); Ryosuke Takahashi, Kyoto (JP); Makoto Higuchi, Chiba (JP); Bin Ji, Chiba (JP); Tetsuya Suhara, Chiba (JP)

(73) Assignees: KYOTO UNIVERSITY, Kyoto-Shi (JP); NATIONAL INSTITUTE OF RADIOLOGICAL SCIENCES, Chiba-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/585,922

(22) Filed: Dec. 30, 2014

(65) Prior Publication Data

US 2015/0266937 A1    Sep. 24, 2015

Related U.S. Application Data

(63) Continuation of application No. 13/520,968, filed as application No. PCT/JP2011/050616 on Jan. 11, 2011, now Pat. No. 8,945,576.

(30) Foreign Application Priority Data

Jan. 8, 2010 (JP) ................................. 2010-003424

(51) Int. Cl.
| | |
|---|---|
| A61K 39/00 | (2006.01) |
| A61K 38/00 | (2006.01) |
| A61K 38/16 | (2006.01) |
| C07K 14/47 | (2006.01) |

(52) U.S. Cl.
CPC ......... *C07K 14/4711* (2013.01); *A61K 39/0005* (2013.01); *A61K 39/0007* (2013.01); *A61K 2039/5256* (2013.01); *A61K 2039/53* (2013.01); *C07K 2319/02* (2013.01); *C12N 2799/021* (2013.01)

(58) Field of Classification Search
None
See application file for complete search history.

(56) References Cited

U.S. PATENT DOCUMENTS

| | | | |
|---|---|---|---|
| 2008/0050383 | A1 | 2/2008 | Sigurdsson et al. |
| 2009/0004144 | A1 | 1/2009 | Tabira et al. |
| 2009/0170798 | A1 | 7/2009 | Hara et al. |

FOREIGN PATENT DOCUMENTS

| | | |
|---|---|---|
| JP | 2005-21149 A | 1/2005 |
| JP | 2008-536476 A | 9/2008 |

OTHER PUBLICATIONS

Rosenmann 2006 "Tauopathy-like abnormalities and neurologic deficits in mice immunized with neuronal tau protein" Arch neurol 63:1459-1467.*
Weiner Nov. 15, 2013 "Reply to Office Action of Aug. 15, 2013" submitted in U.S. Appl. No. 13/520,968.*
Final Office Action dated Feb. 12, 2014, issued in U.S. Appl. No. 13/520,968.
International Search Report, issued in PCT/JP2011/050616, filed on Mar. 8, 2011.
Non-Final Office Action dated Aug. 15, 2013, issued in U.S. Appl. No. 13/520,968.
Notice of Allowance dated Sep. 18, 2014, issued in U.S. Appl. No. 13/520,968.
Okura et al., "Recent advance in immunotherapies for Alzheimer disease: with special reference to DNA vaccination", Human Vaccines, Jun. 2009, vol. 5, No. 6, pp. 373-380.
Rafii and Aisen 2009 "Recent developments in Alzheimers disease therapeutics" BMC medicine 7(7):1-4.
Zhou et al., "Alternative splicing of exon 10 in the tau gene as a target for treatment of tauopathies", BMC Neuroscience, 2008, vol. 9, supple. 2, S10, pp. 1-8.

* cited by examiner

*Primary Examiner* — Adam M Weidner
(74) *Attorney, Agent, or Firm* — Birch, Stewart, Kolasch & Birch, LLP

(57) ABSTRACT

This invention relates to a vaccine for preventing or treating tautopathy, comprising a vector, as an active ingredient, comprising a nucleic acid encoding a mutant tau protein linked to a secretion signal sequence, wherein the vaccine is capable of inducing an antibody against an (optionally phospholylated) tau protein in a subject in a more sustained manner compared with a case where the mutant tau protein is administered directly.

5 Claims, 28 Drawing Sheets
(6 of 28 Drawing Sheet(s) Filed in Color)

Fig. 7
A
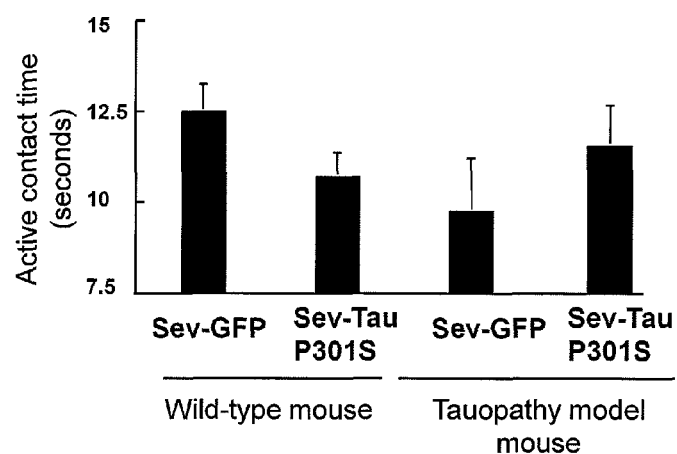
B
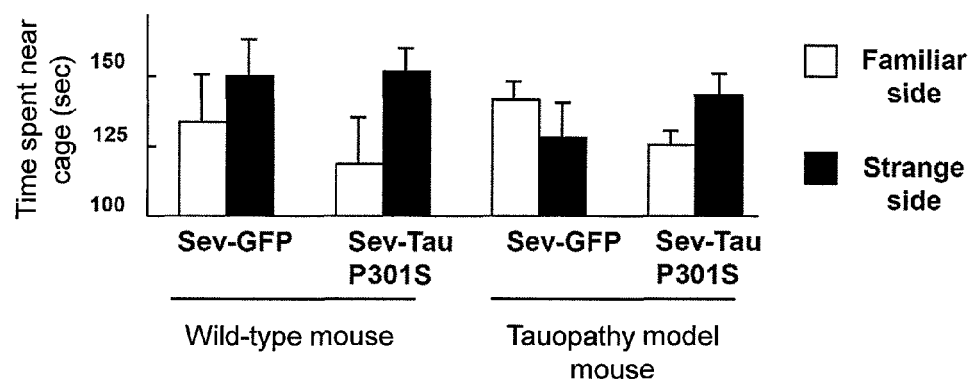

Fig. 12
A
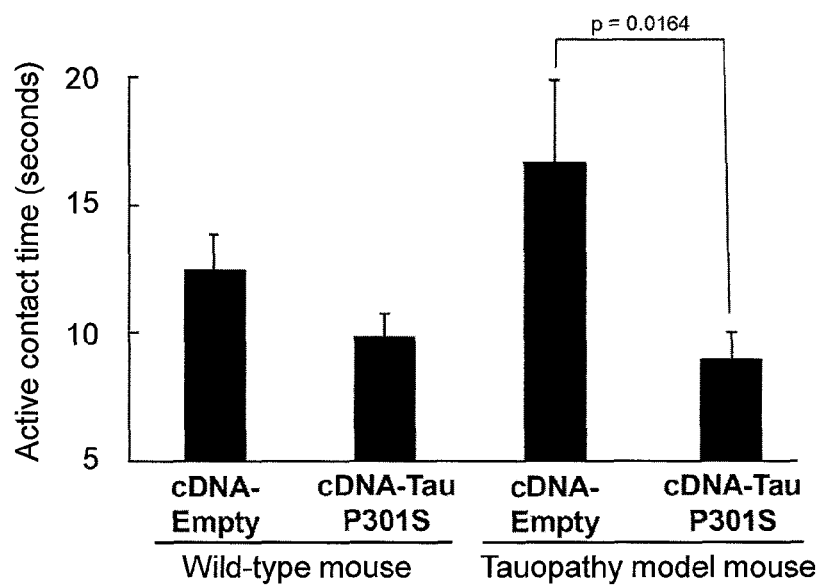
B
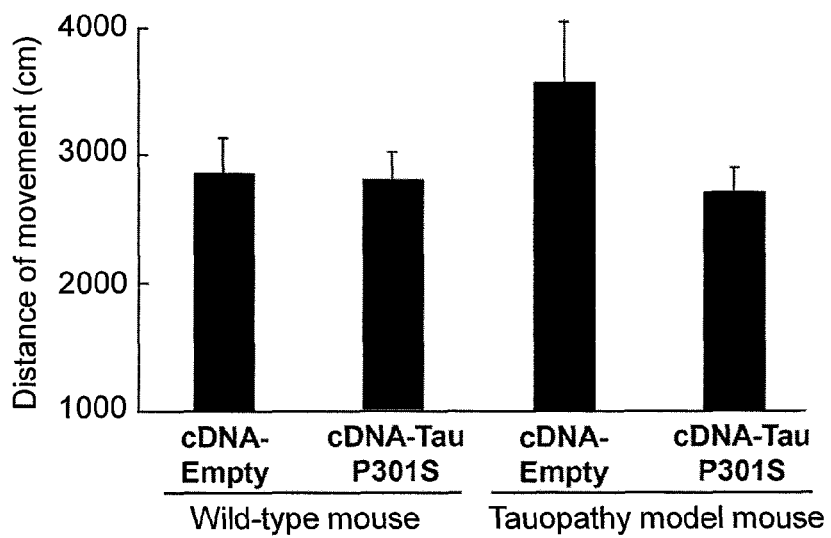

Fig. 13 pcDNA3.1-CD59-Tau P301S (ATG-)

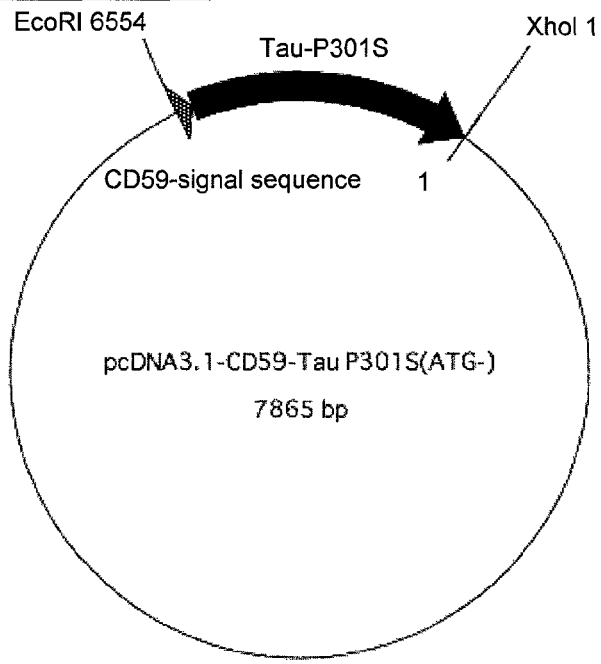

Plasmid name: pcDNA3.1-CD59-Tau P301S(ATG-)
Plasmid size: 7865 bp

EcoRI  kozak  →CD59 signal sequence (NT_009237.18)
gaattcgccaccATGGGAATCCAAGGAGGGTCTGTCCTGTTCGGGCTGCTGCTCGTCCTGGCTGTCTTCTGC
           →Tau P301S
CATTCAGGTCATAGCgctgagccccgccaggagttcgaagtgatggaagatcacgctggg
acgtacgggttgggggacaggaaagatcaggggggctacaccatgcaccaagaccaagag
ggtgacacggacgctggcctgaaagaatctcccctgcagaccccactgaggacggatct
gaggaaccgggctctgaaacctctgatgctaagagcactccaacagcggaagctgaagaa
gcaggcattggagacaccccagcctggaagacgaagctgctggtcacgtgacccaagct
cgcatggtcagtaaaagcaaagacgggactggaagcgatgacaaaaaagccaaggggct
gatggtaaaacgaagatcgccacaccgcggggagcagcccctccaggccagaagggccag
gccaacgccaccaggattccagcaaaaacccgcccgctccaaagacaccacccagctct
ggtgaacctccaaaatcaggggatcgcagcggctacagcagccccggctccccaggcact
cccggcagccgctcccgcaccccgtcccttccaacccacccaccgggagcccaagaag
gtggcagtggtccgtactccacccaagtcgccgtcttccgccaagagccgcctgcagaca
gcccccgtgcccatgccagacctgaagaatgtcaagtccaagatcggctccactgagaac
ctgaagcaccagccgggaggcgggaaggtgcagataattaataagaagctggatcttagc
aacgtccagtccaagtgtggctcaaaggataatatcaaacacgtcagtggaggcggcagt
gtgcaaatagtctacaaaccagttgacctgagcaaggtgacctccaagtgtggctcatta
ggcaacatccatcataaaccaggaggtggccaggtggaagtaaaatctgagaagcttgac
ttcaaggacagagtccagtcgaagattgggtccctggacaatatcacccacgtccctggc
ggaggaaataaaaagattgaaacccacaagctgaccttccgcgagaacgccaaagccaag
acagaccacggggcggagatcgtgtacaagtcgccagtggtgtctggggacacgtctcca
cggcatctcagcaatgtctcctccaccggcagcatcgacatggtagactcgccccagctc
gccacgctagctgacgaggtgtctgcctccctggccaagcagggttttgtga
                                                  stop

VACCINE FOR TREATMENT OF TAUTOPATHY

This application is a Continuation of application Ser. No. 13/520,968, filed on Jul. 6, 2012, which was filed as PCT International Application No. PCT/JP2011/050616 on Jan. 11, 2011, which claims priority under 35 U.S.C. §119(a) to Japanese Patent Application No. 2010-003424, filed in Japan on Jan. 8, 2010, all of which are hereby expressly incorporated by reference into the present application.

TECHNICAL FIELD

The present invention relates to a vector capable of expressing a mutant tau protein, usable for preventing or treating tauopathy, and the use thereof as a pharmaceutical agent.

BACKGROUND ART

Tau protein is a soluble phosphorylated protein present in a state of binding to intracellular microtubules in the normal brain, contributes to the promoted polymerization and stabilization of the microtubules, and maintains an equilibrium state while repeating binding to and dissociation from the microtubules. The break-down of the equilibrium state due to phosphorilation/dephosphorylation enzyme abnormality or the like increases free tau protein in the cytoplasm and leads to the aggregation or fibrosis thereof. In the majority of dementias in elderly people, including Alzheimer's disease and frontotemporal dementia, neurodegenerative diseases in which the accumulation of tau protein aggregates without always the accumulation of amyloid is observed as a characteristic lesion are collectively called tauopathy (Non Patent Literature 1).

In Japan, dementia is seen in about 7% of elderly people 65 or older, and the prevalence reaches about 10% when mild dementia is included. Seventy percent thereof is said to have tauopathy dementia, and the number of the patients is about 2,000,000. In the research and development on dementia, research has previously been ahead on amyloid β (Aβ) protein, a clinical trial using immunization with a peptide from amyloid β has been conducted; however, the trial has been discontinued because meningoencephalitis occurred in 6% of patients inoculated therewith midway through the trial (Non Patent Literature 2). Although the trial has been discontinued, it has been confirmed that the vaccination had the effect of eliminating senile plaques and degenerative nerve projections, from a case report on a patient who developed, and recovered from, encephalitis after the vaccination and then died from another disease (Non Patent Literature 3). The subsequent follow-up study of the vaccinated patient also determined that the disease progressed even in the patient in whom the disappearance of senile plaques was confirmed by autopsy after the vaccination, suggesting that the vaccine had no effect of preventing the progression of the disease (Non Patent Literature 4).

Previous studies have also shown that passive immunity with an antibody to amyloid is effective; however, the effect of suppressing the progression of the disease has not been elucidated (Non Patent Literature 5).

In addition, the effect of an oral vaccine was tested in which an adeno-associated virus (AAV) vector carried amyloid β. The oral administration of the AAV vector was observed to have the effect of producing an antibody to amyloid β via the intestinal mucosa and the effect of improving a learning function in experiments using mice (Non Patent Literature 6); however, in the subsequent experiment using monkeys, it was observed to decrease senile plaques but was not confirmed to have a definite effect of suppressing the progression of the disease.

In contrast, importance has previously been poorly attached to tau protein as a target for the treatment of Alzheimer's disease and the like; however, the tau protein is more recently becoming a target for the treatment of, and a vaccine for, tauopathy accompanied by the excess accumulation of the tau protein, as a target for a therapeutic agent for Alzheimer's disease (Non Patent Literature 7).

Reported therapeutic agents related to the present invention include therapeutic agents for Alzheimer disease, in which an adeno-associated virus carried a gene encoding amyloid 13 (Patent Literatures 1 and 2 and Non Patent Literature 8), and methods for treating Alzheimer disease and tauopathy by inoculating tau protein (Patent Literature 3 and Non Patent Literature 9); however, the effects of improving coordinated movement and motor learning were observed in tauopathy model mice inoculated with tau protein but there were not observed the effects of improving the symptoms characteristically seen in dementia patients of unsociability and reduced recent memory.

PRIOR ART LITERATURE

Patent Literature 1
  JP Patent Publication (Kohyo) No. 2008-536476
Patent Literature 2
  JP Patent Publication (Kokai) No. 2005-021149
Patent Literature 3
  US 2008/0050383A
Non Patent Literature 1
  Hiroko Saito, Rinsho Kensa (Clinical Examination), 50 (10): 1121-1129 (2006) (Japan)
Non Patent Literature 2
  Orgogozo, J. M. et al., Neurology, 61: 46-54 (2003)
Non Patent Literature 3
  Nicoll, J. A. et al., Nature Medicine, 9: 448-452 (2003)
Non Patent Literature 4
  Holmes, C. et al., Lancet, 372: 216-223 (2008)
Non Patent Literature 5
  Yasuji Matsuoka, Jikken Igaku (Experimental Medicine), 26 (16): 2572-2576 (2008) (Japan)
Non Patent Literature 6
  Takeshi Tahira, Ronen Seishin-Igaku Zasshi (Journal of Geriatric Psychiatry) 20 (Extra issue): 68-74 (2009) (Japan)
Non Patent Literature 7
  Martin-Jones, Z and Lasagna-Reeves, C., Alzheimer Disease Associate Disorder, 22 (2): 111 (2008)
Non Patent Literature 8
  Mouri, A. et al., The FASEB Journal, 21: 2135-2148 (2007)
Non Patent Literature 9
  Asuni, A. A. et al., J. Neurosci., 27: 9115-9129 (2007)

SUMMARY OF INVENTION

An object of the present invention is to provide a vaccine for preventing or treating tauopathy, especially tauopathy dementia.

The present inventors have now confirmed in a test using tauopathy model mice that a vector comprising a nucleic acid encoding a mutant tau protein has a long sustained antibody-inducing action compared to the protein itself, and have now further found that the vector has an action of significantly improving tauopathy, especially tauopathy dementia, thereby accomplishing the present invention.

Thus, in summary, the present invention encompasses the following features.

A first aspect of the present invention provides a vaccine for preventing or treating tauopathy, comprising a vector, as an active ingredient, comprising a nucleic acid encoding a mutant tau protein linked to a secretory signal sequence, wherein the mutant tau protein comprises the mutation of an amino acid residue at a position corresponding to at least one position selected from the group consisting of positions 257, 260, 266, 272, 279, 280, 284, 296, 301, 303, 305, 315, 317, 320, 335, 336, 337, 342, 352, 369, 389, and 406 of SEQ ID NO: 1 in the amino acid sequence of tau protein, and wherein the vector is capable of inducing an antibody to (optionally phosphorylated) tau protein in a subject in a more sustained manner compared with a case where the mutant tau protein is administered directly.

In an embodiment thereof, the mutation is at least one mutation selected from the group consisting of K257T, I260V, L266V, G272V, N279K, K280Δ, L284L, N296Δ, N296H, P301L, P301S, P301T, G303V, S305N, L315R, K317M, S320F, G335S, G335V, Q336R, V337M, E342V, S352L, K369I, G389R, and R406W, where Δ represents a deletion.

In another embodiment, the mutation comprises at least a mutation of P301L, P301S, or P301T.

In another embodiment, the secretory signal sequence is a signal sequence of amyloid precursor protein or a secretory signal sequence of CD59.

In another embodiment, the vector is a Sendai virus vector.

In another embodiment, the vector is a plasmid vector.

In another embodiment, the vaccine is formulated for intranasal administration.

In another embodiment, the vaccine has an effect of improving tauopathy dementia.

In another embodiment, the vaccine has an effect of improving at least one symptom of reduced recent memory and/or abnormal social interaction, abnormal anxiety-like behavior, and impaired memory in a subject.

In another embodiment, the vaccine has an effect of activating microglia in the brain of the subject and thereby suppressing the accumulation of the mutant tau protein.

In another embodiment, the tau protein (including the mutant tau protein) is optionally phosphorylated.

The vaccine of the present invention has the effect of significantly improving reduced recent memory and/or abnormal social interaction and/or abnormal anxiety-like behavior and/or impaired memory in dementia in a subject with tauopathy, and especially has an action of suppressing (or retarding) the progression of symptoms of tauopathy, against which conventional vaccines have not been effective.

The present specification encompasses the contents of the specification and/or drawings of Japanese Patent Application No. 2010-3424, from which the present application claims the priority.

BRIEF DESCRIPTION OF DRAWINGS

The patent or application file contains at least one color drawing. Copies of this patent or patent application publication with color drawing will be provided by the USPTO upon request and payment of the necessary fee.

Non-Tg/Sev-GFP: a group in which wild-type mice were nasally inoculated with Sev-GFP, Non-Tg/Sev-TauP301S: a group in which wild-type mice were nasally inoculated with Sev-TauP301S, Tg/Sev-GFP: a group in which tauopathy model mice were nasally inoculated with Sev-GFP, Tg/Sev-TauP301S: a group in which tauopathy model mice were nasally inoculated with Sev-TauP301S, −: a negative control (a protein extracted from wild-type mice), and +: a positive control (a protein extracted from the hippocampus of tauopathy model mice to which nothing was administered).

Figure 4:
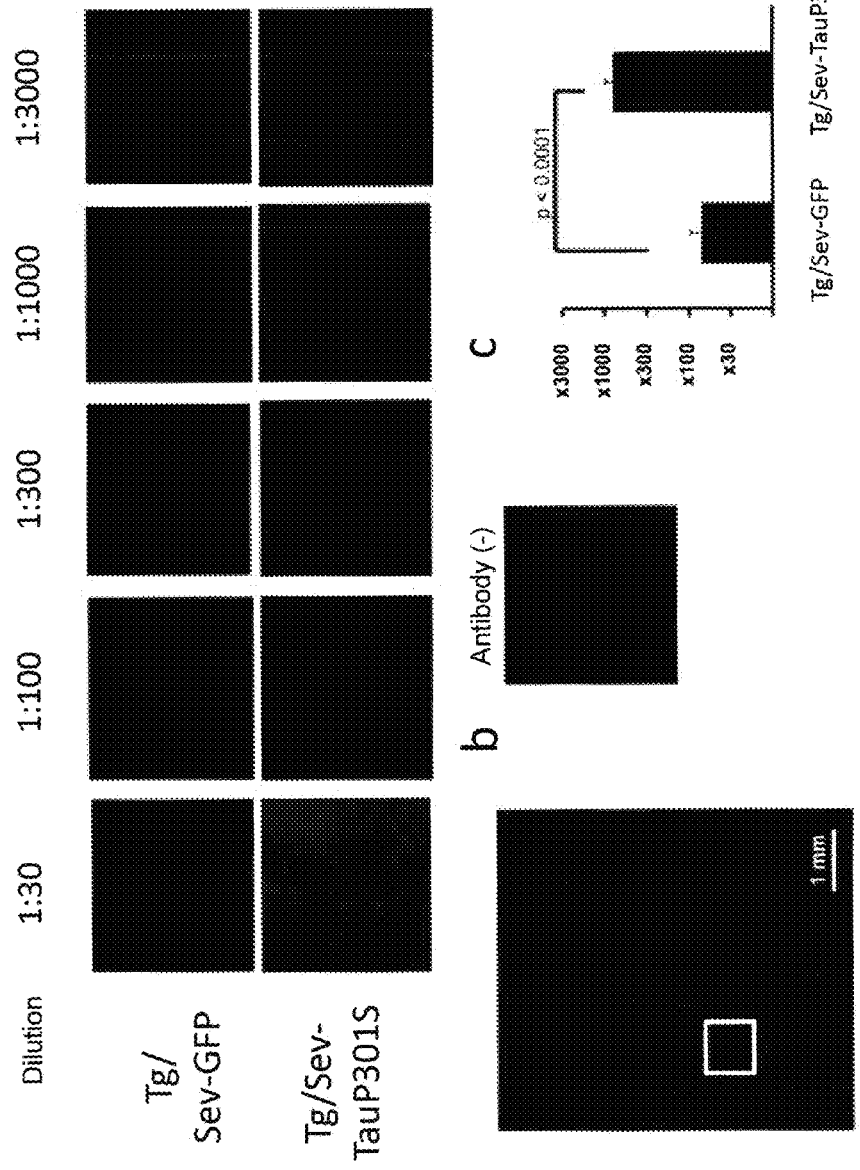

FIG. 4 shows that the antibody produced in the serum by the inoculation of Sev-TauP301S reacted with the hippocampus expressing phosphorylated tau. More specifically, (a) is a series of photographs showing the results of inoculating tauopathy model mice or wild-type mice with Sev-TauP301S before collecting sera and evaluating the antibody titer in each serum reacting with tissue tau based on reactivity in the hippocampal tissue (a white box portion) of a corresponding mouse.

The serum of each mouse to which Sev-TauP301S was administered was diluted 30 times, 100 times, 300 times, 1,000 times, or 3,000 times, reacted therewith at 4° C. overnight, and reacted with an Alexa546-labeled anti-mouse IgG antibody as a secondary antibody at room temperature for 1 hour.

(b) is a photograph showing the result of performing immunostaining without reaction with the antibody in tauopathy model mice as control.

(c) is a graph showing the results of evaluating the antibody titer in the serum of each tauopathy model mouse inoculated with Sev-GFP or Sev-TauP301S by the maximum dilution at which the reaction with the tissue was observed.

The mean±standard error was calculated for each of the Sev-GFP-inoculated group and the Sev-TauP301S-inoculated group, and statistical analysis was performed by Mann-Whitney U test.

Figure 5:
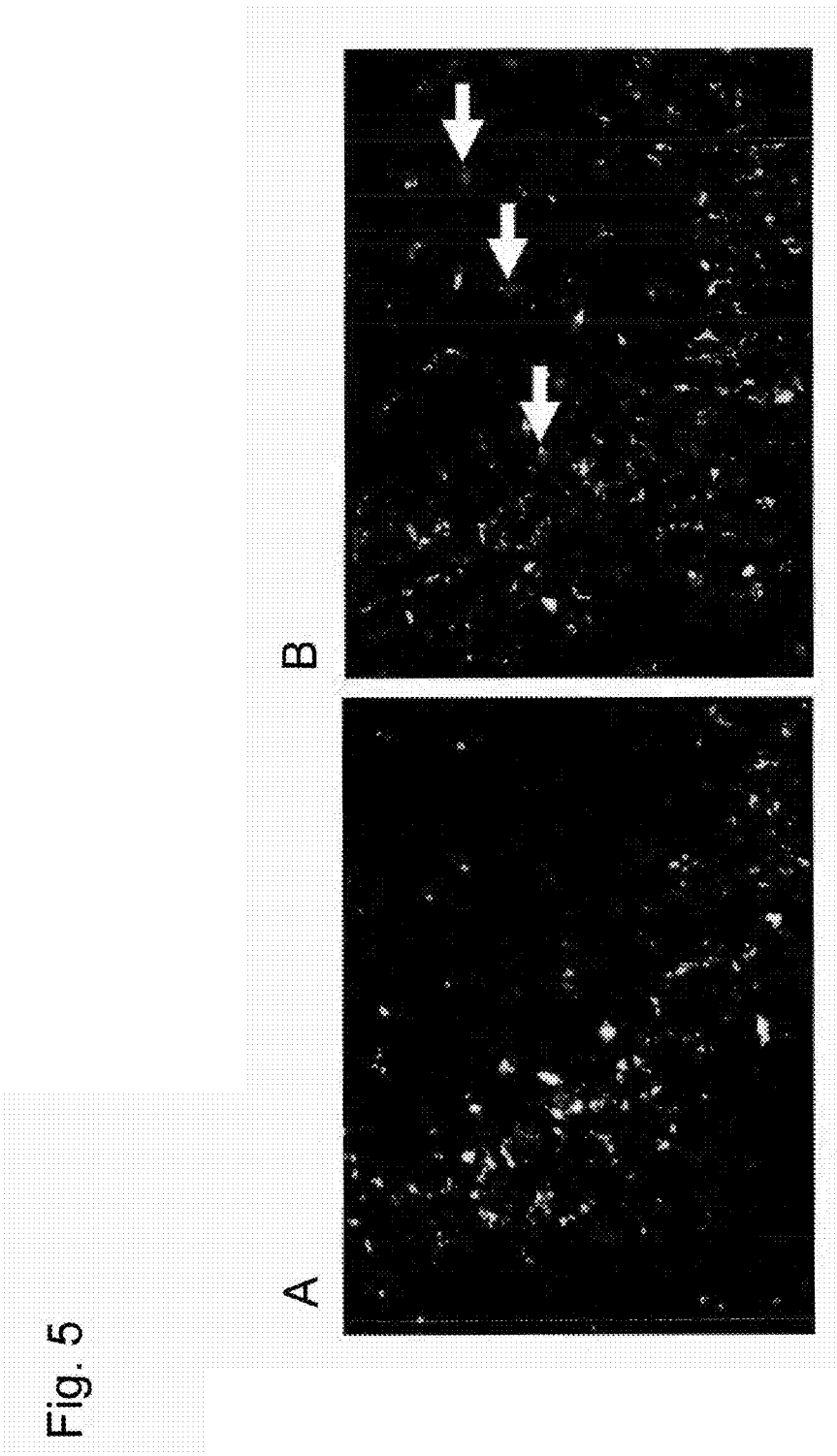

FIG. 5 is a pair of photographs showing the results of analyzing the activation of microglia in the brain by inoculation with Sev-TauP301S. Sev-TauP301S was inoculated, and 5 months after administration, immunostaining was carried out using an anti-Iba1 antibody capable of recognizing the activated microglia in the tissue of the mouse hippocampus (A). Sev-GFP was inoculated as a control (B). The arrow indicates microglia not coexistent with IgG.

Figure 6:
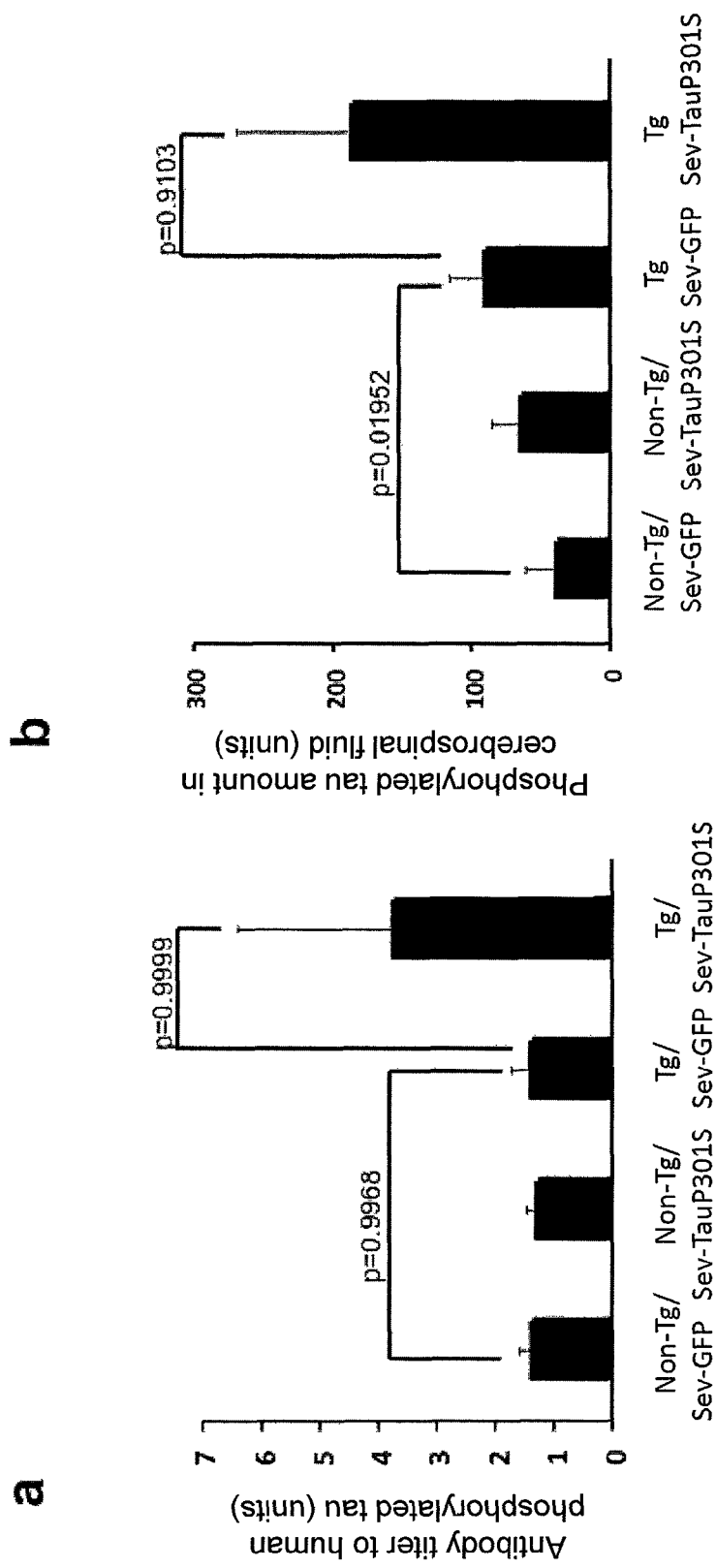

FIG. 6 is a pairs of graphs showing the results of analyzing the production of an anti-phosphorylated tau antibody in the serum and the production of phosphorylated tau protein in the cerebrospinal fluid after inoculating Sev-GFP or Sev-TauP301S into wild-type mice or tauopathy model mice. The analysis of the antibody production was carried out by ELISA with a recombinant mutant tau protein (TAUP301S) as an antigen using the serum of mice inoculated with Sev-GFP or Sev-TauP301S.

For the phosphorylated tau protein production, ELISA by binding to an anti-phosphorylated tau antibody (AT8 antibody) was carried out using the cerebrospinal fluid of mice inoculated with Sev-GFP or Sev-TauP301S.

(a) shows an antibody titer to human P301S mutant protein in the serum on the 5th month after inoculation with Sev-GFP or Sev-TauP301S.

(b) shows the amount of phosphorylated tau in CSF on the 5th month after inoculation with Sev-GFP or Sev-TauP301S.

FIG. 7 shows social interaction tests. More specifically (A) is a graph showing the results of inoculating Sev-GFP or Sev-TauP301S into wild-type mice or tauopathy model mice and performing a social interaction test. The "social interaction test" (in which 2 mice was placed in a box and the contact time therebetween was measured for 10 minutes) on social interaction was carried out because abnormal social interaction was frequently observed in tauopathy patients. (B) is a graph showing the results of further evaluating with how much interest a mouse tries to make closer approach to a strange mouse by measuring the time spent around near a cage (containing the strange mouse) in Crawley's Social Interaction test (recent memory and social interaction test).

Figure 8:
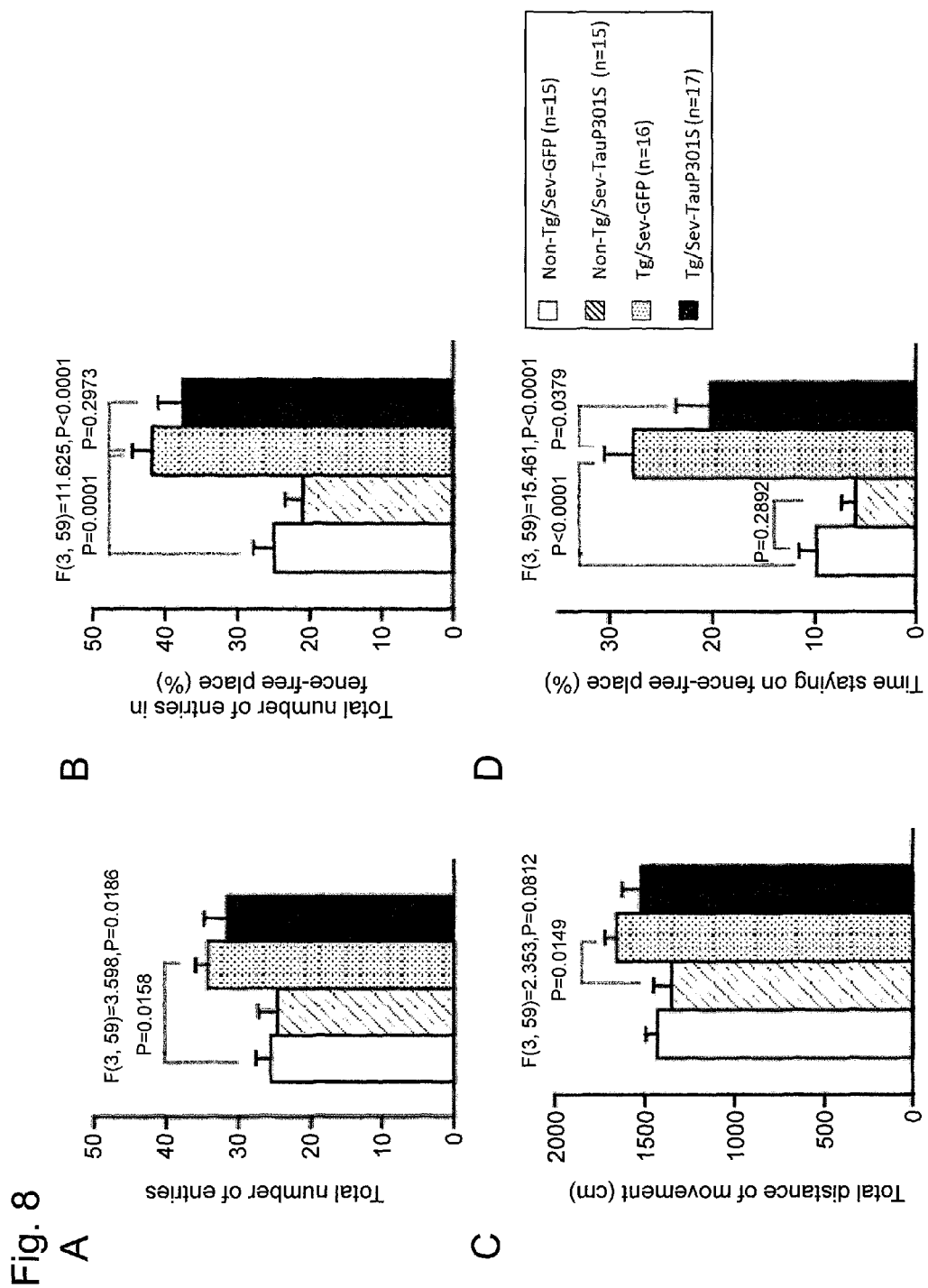

FIG. 8 is a series of graphs showing the results of inoculating Sev-GFP or Sev-TauP301S into wild-type mice or tauopathy model mice and performing an elevated plus maze test (test of anxiety-like behavior). In each of the Sev-TauP301S or Sev-GFP-inoculated mice, the total number of entries in each of the 4 directions from the middle of the maze (A), the percentage of the number of entries in the directions of the absence of fences (B), the total distance of movement of each mouse (C), and the percentage of the time spent in the fence-free place (D) were observed for 10 minutes and automatically measured using Image EP software. Statistical analysis was performed by one-way ANOVA, and a post hoc test was carried out by Fisher's Protected Least Significant Difference (PLSD) method.

Figure 9:
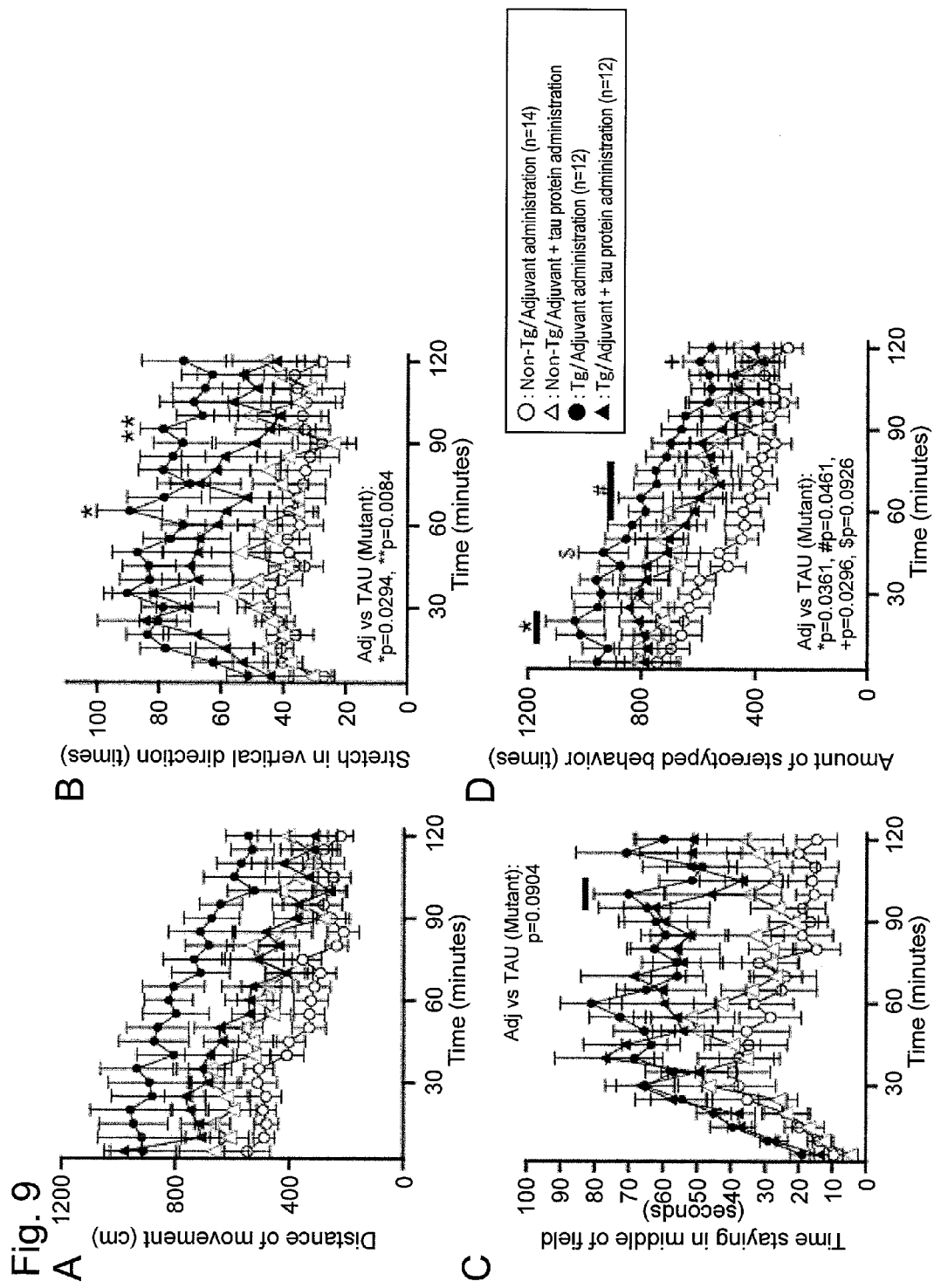

FIG. 9 is a series of graphs showing the results of inoculating a recombinant tau protein into wild-type mice or tauopathy model mice and performing an open field test (a test for measuring the amount of activity and emotionality). Recombinant tau protein (TAUP301S) was inoculated, and on the 1st month after inoculation, the open field test was carried out. Free movement was observed for 120 minutes for the distance of movement of the inoculated mice (A), the number of stretches (B), the time staying on the middle of the field (C), and stereotyped behavior (D) for evaluation.

Figure 10:
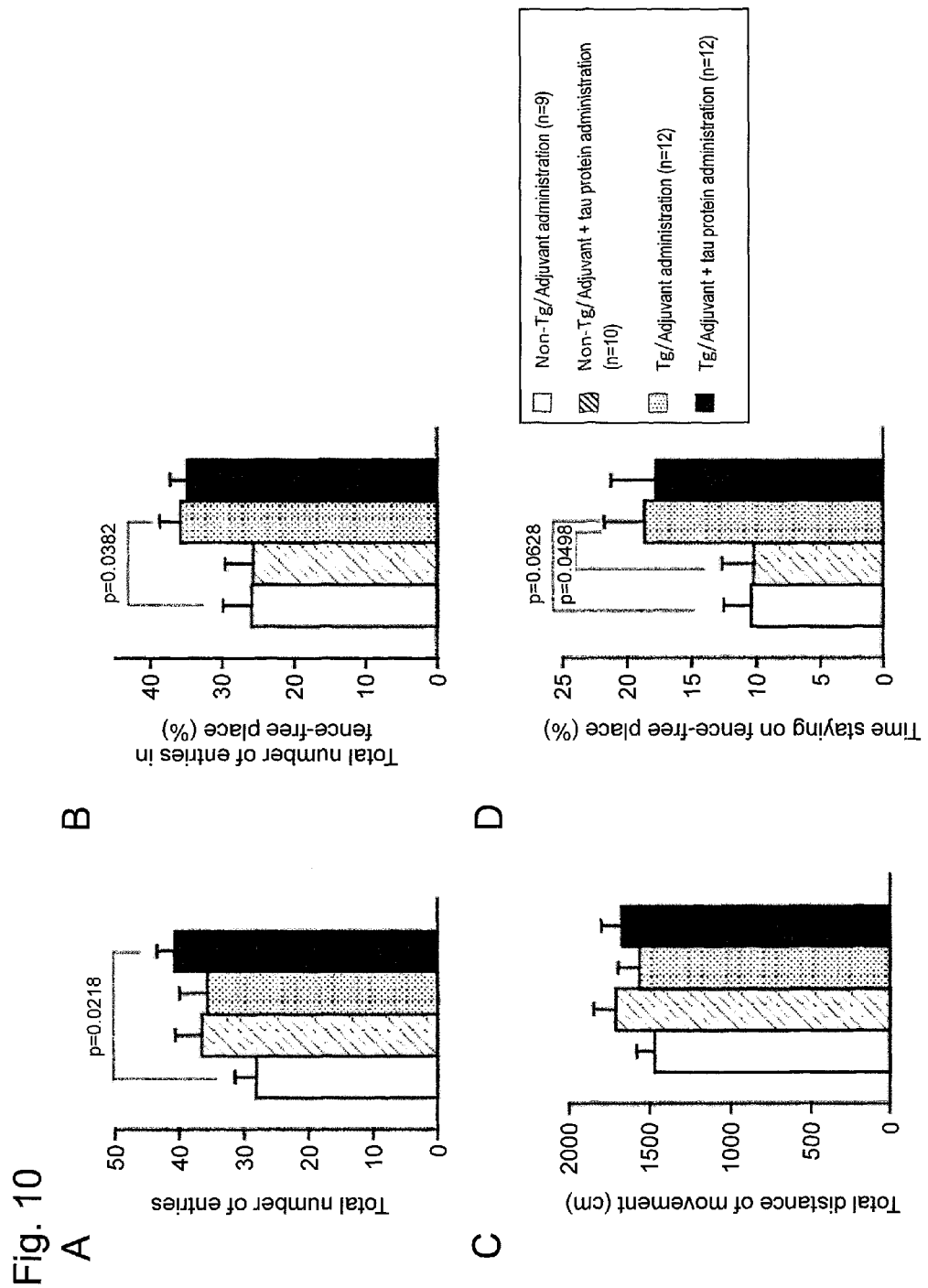

FIG. 10 is a series of graphs showing the results of inoculating a recombinant tau protein into wild-type mice or tauopathy model mice and performing an elevated plus maze test (test of anxiety-like behavior). Tauopathy model mice or wild-type mice subcutaneously inoculated with 100 µg/animal per administration of recombinant tau protein (TAUP301S) 3 times in total every 2 weeks were each placed to face toward a closed arm in a square portion (5×5 cm) in the center of the maze and recorded for behavior for 10 minutes. Sev-GFP was inoculated as a control. The total number of entries in each of the four directions from the middle (A), the percentage of the number of entries in the directions of the absence of fences (B), the total distance of movement of each mouse (C), and the percentage of the time staying in the fence-free place (D) were automatically measured using Image EP software. Statistical analysis was performed by one-way ANOVA, and a post hoc test was carried out by Fisher's Protected Least Significant Difference (PLSD) method.

Figure 11:
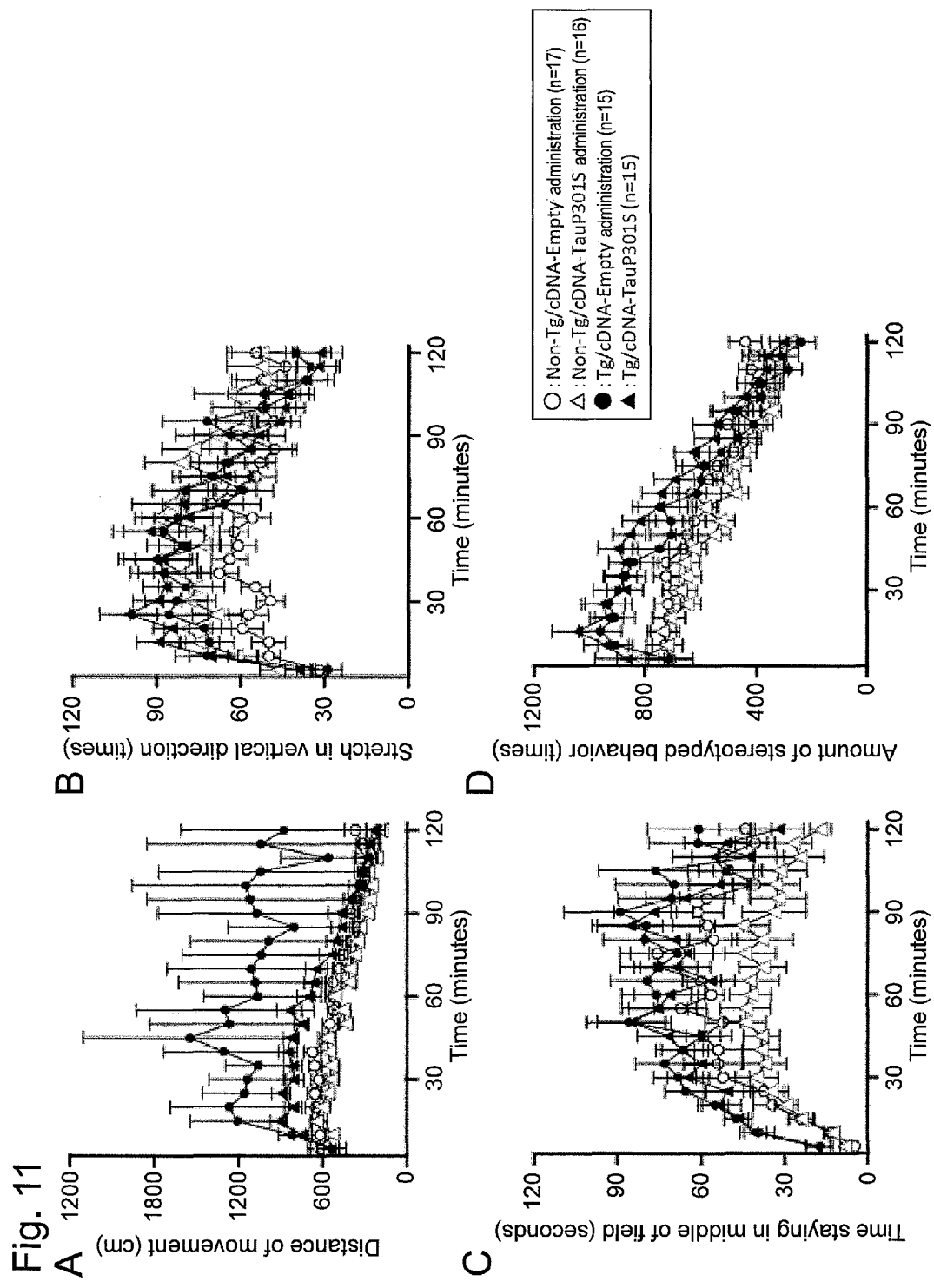

FIG. 11 is a series of graphs showing the results of inoculating pcDNA3.1-CD59-Tau P301S (ATG-) (hereinafter referred to as cDNA-Tau P301S) into wild-type mice or tauopathy model mice and performing an open field test. On the 1st month after inoculation of cDNA-Tau P301S, the open field test was carried out. Free movement was observed for 120 minutes for the distance of movement of the inoculated mice (A), the number of stretches (B), the time staying on the middle of the field (C), and stereotyped behavior (D) for evaluation.

FIG. 12 is a pair of graphs showing the results of inoculating cDNA-Tau P301S into wild-type mice or tauopathy model mice and performing a social interaction test. The "social interaction test" (in which 2 mice was placed in a box and the contact time therebetween was measured for 10 minutes) on social interaction was carried out because abnormal social interaction was frequently observed in tauopathy patients.

FIG. 13 is a drawing showing the structure of cDNA-Tau P301S and the insertion sequence (SEQ ID NO: 12).

Figure 14:
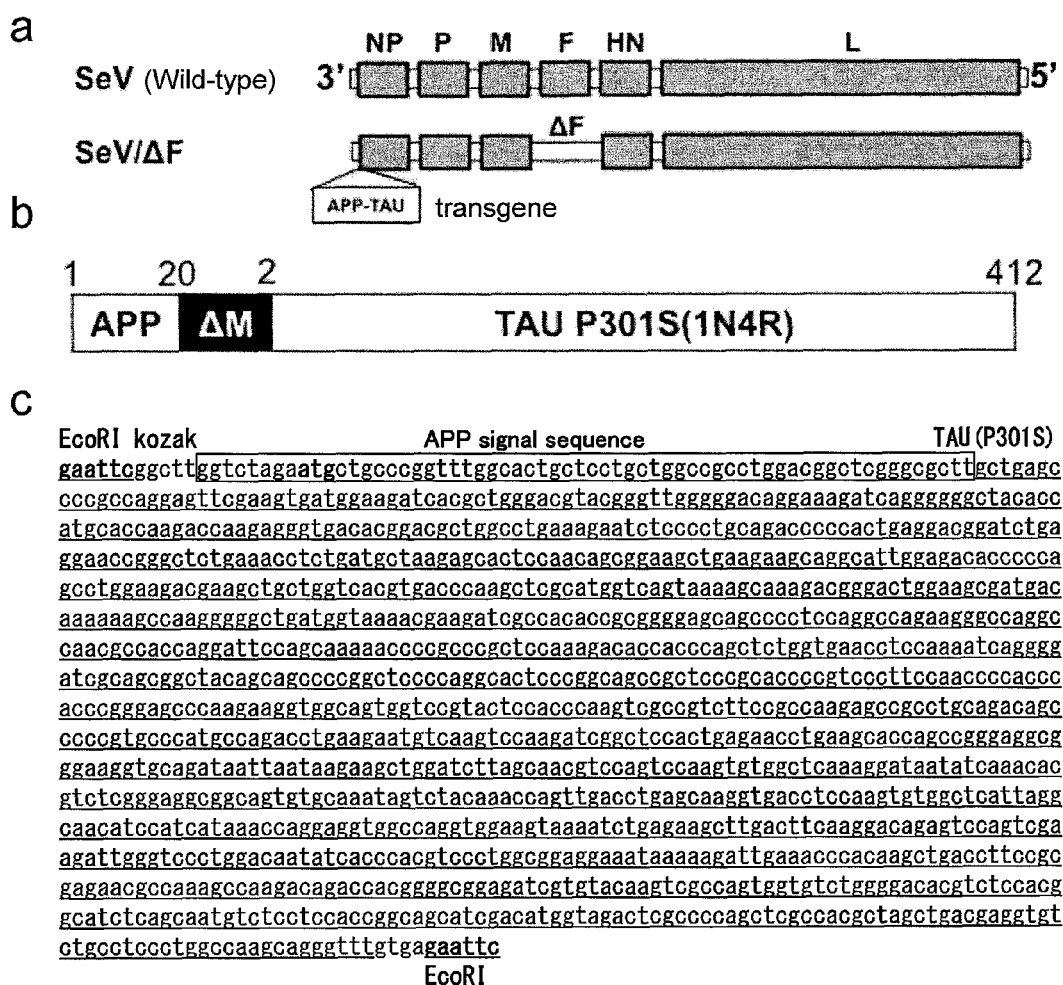

FIG. 14 shows actually constructed plasmid for reconstituting the Sendai virus vector. More specifically, (a) is a diagram showing a mutation at the 301st amino acid residue of the longest isoform of tau protein with respect to P301S. Sev/ΔF shows Sendai virus whose F gene is deleted. (b) is a diagram showing the signal sequence of amyloid precursor protein (APP) connected to the N-terminal end of a human mutant tau protein (P301S, isoform 1N4R), from which methionine is deleted. (c) is a diagram showing the insertion sequence (SEQ ID NO: 13) in pcDNA3-APP-TauP301S. The APP signal sequence used herein is registered in GenBank under the accession number NT_011512.11, NW_001838706.1, NM_201414.1, NM_201413.1, NM_000484.2, NM_001136130.1, or NM_001136129.1. The sequence of P301S Tau is a mutant of the sequence registered in GenBank under the accession number NM_001123067.2.

Figure 15:
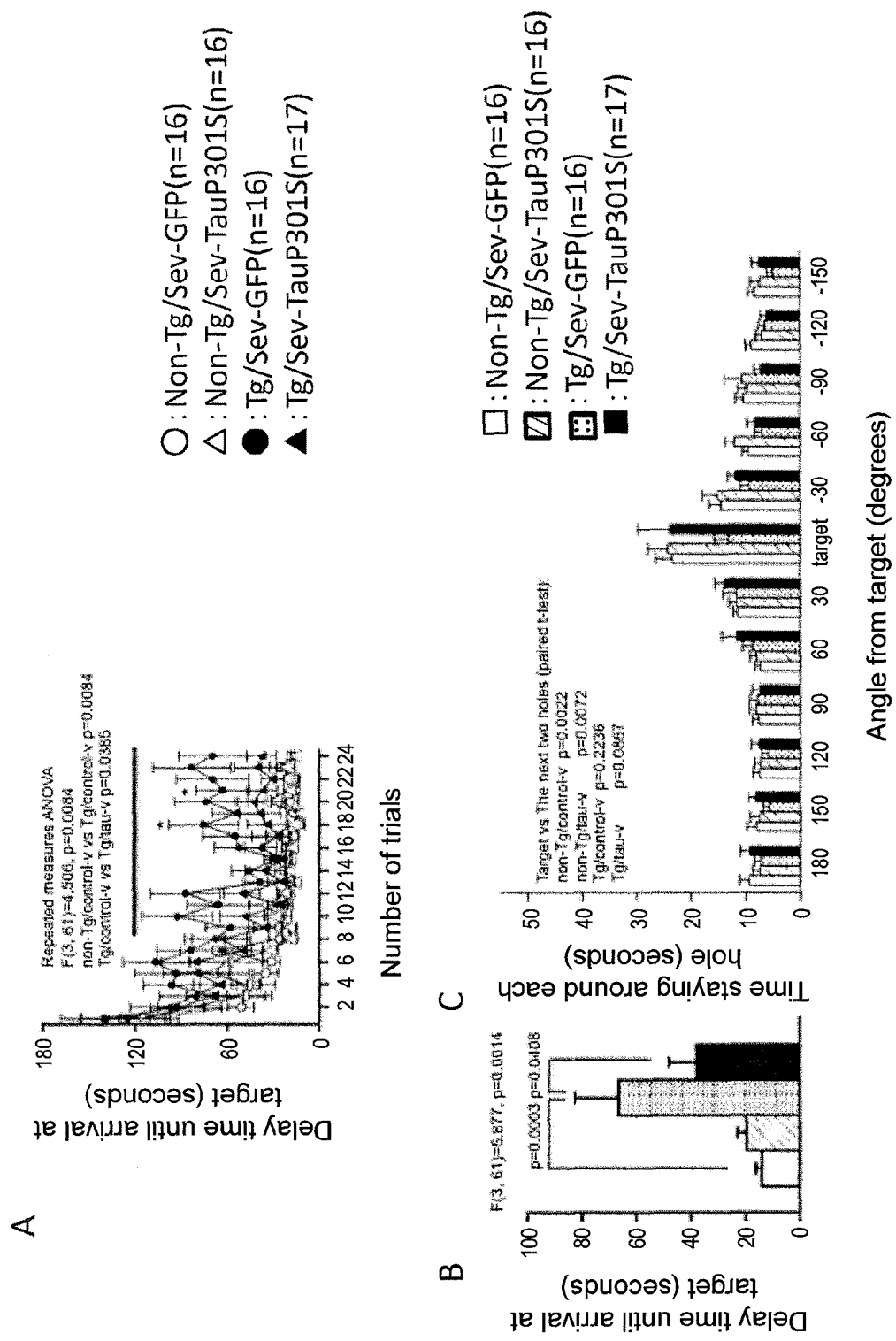

FIG. 15 shows the Barnes Maze Test by Inoculation of Sev-TauP301S into Tauopathy Model Mouse. (A) is a graph showing the results of a Barnes maze test (spacial memory) in wild-type mice and tauopathy model mice inoculated with Sev-GFP or Sev-TauP301S. Mice were each blindfolded by placing in a tube, set in a predetermined position, and allowed to walk freely by removing the tube, and a dark box was attached to the hole of the correct answer to cause the mouse to remember the place in which the dark box was located (training). (B) is a graph showing the results of recording the time staying around the hole (target) from which the dark box was removed, after training (probe test). (C) is a graph that shows further increasing the time staying around the hole as the target confirming an improvement effect.

Measurement was performed of the time until arrive at the target in the training period, the time until arrival at the target in the probe test, and the time staying around each hole.

Figure 16:
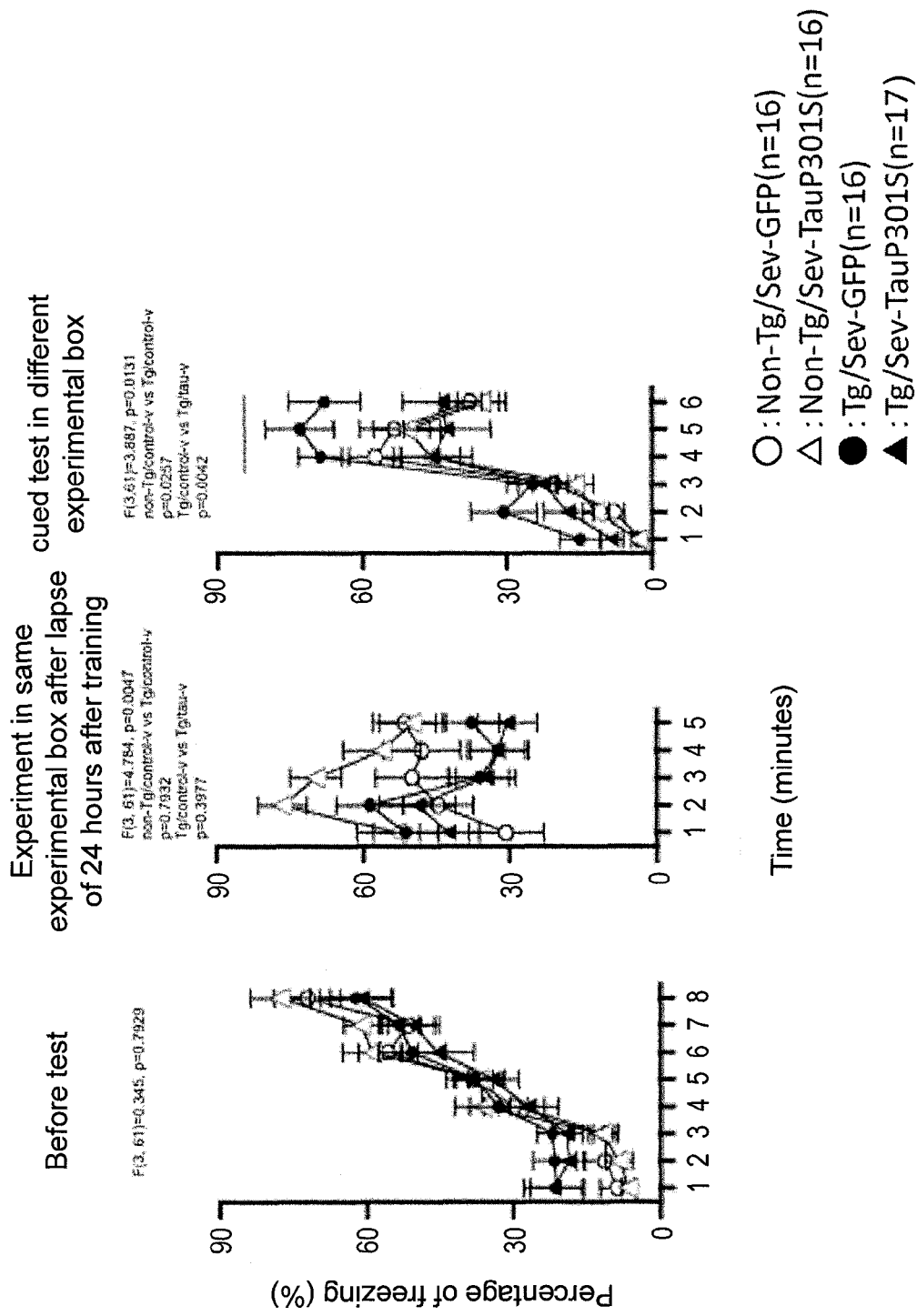

FIG. 16 is a series of graphs showing the results of a conditioned fear test (contextual memory) in wild-type mice and tauopathy model mice inoculated with Sev-GFP or Sev-TauP301S. A combination of a sound and an electroshock was presented to a mouse in a box to condition the mouse, and evaluation was carried out using the percentage of occurrence of freezing caused by again placing in the same box.

Figure 17:
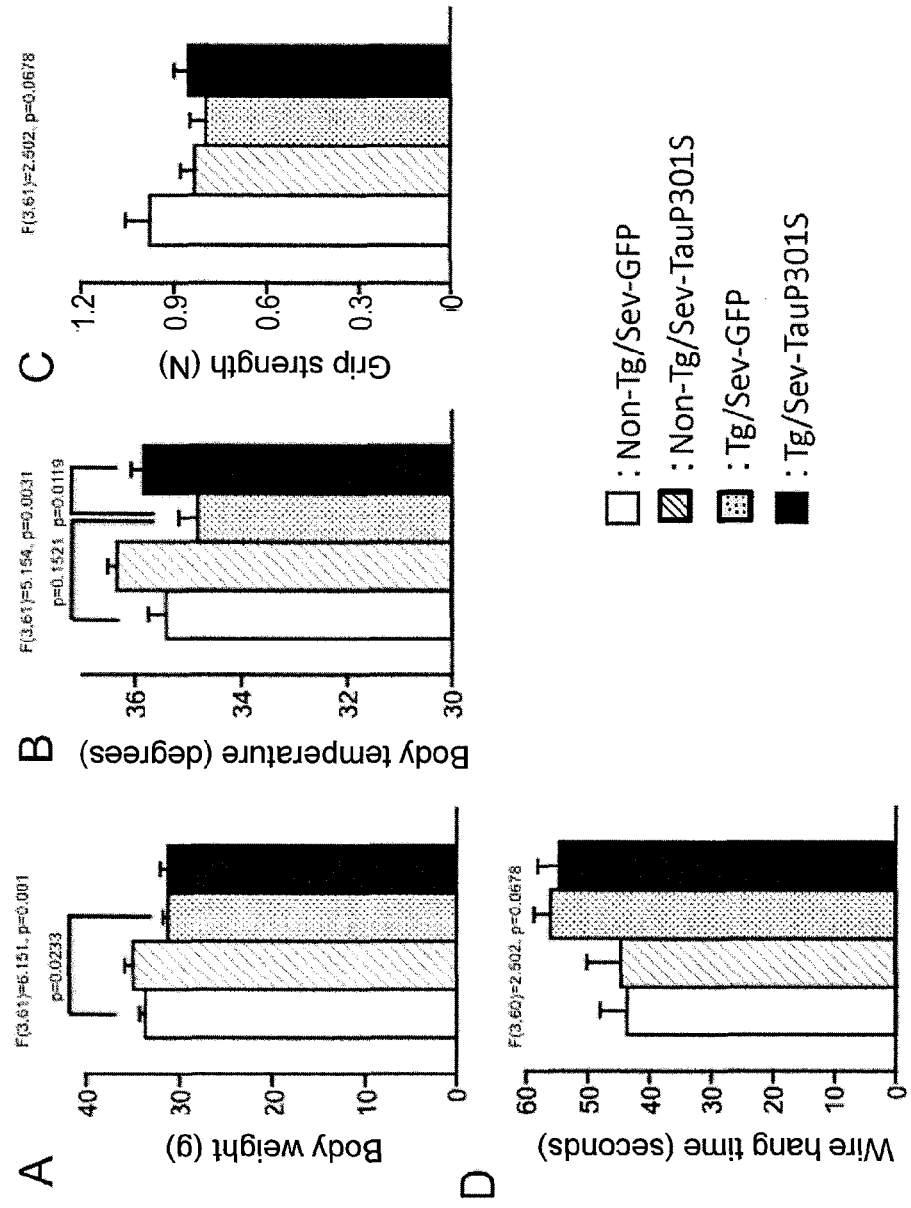

FIG. 17 is a series of graphs showing the results of body measurements (body weight (A), body temperature (B), grip strength (C), and a wire hang test (D)) in wild-type mice and tauopathy model mice inoculated with Sev-GFP or Sev-TauP301S.

Figure 18:
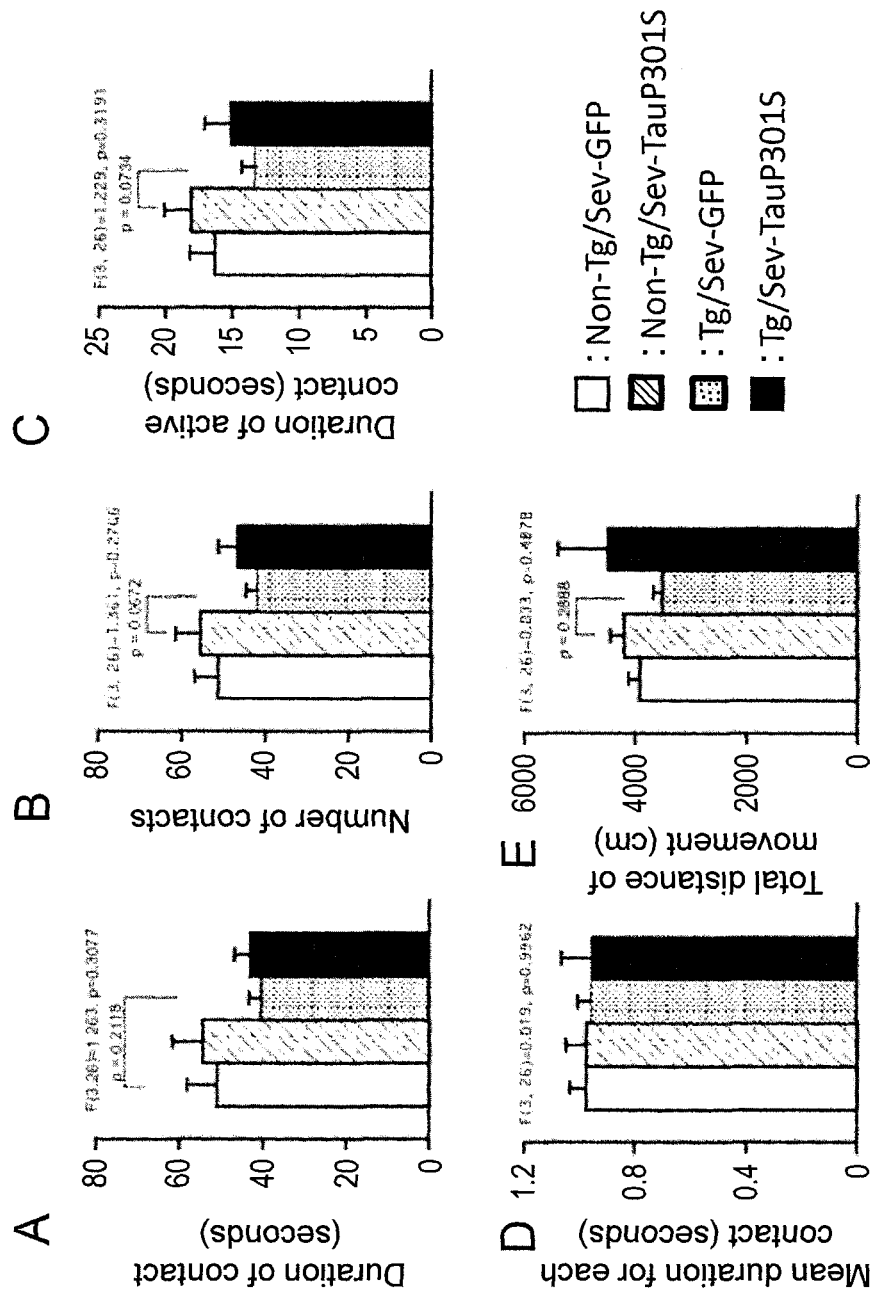

FIG. 18 is a series of graphs showing the results of a social interaction test (the total duration of contact (A), the number of contacts (B), the total duration of active contact (C), the mean value of the duration of contact (D), and the total movement distance (E)) in wild-type mice and tauopathy model mice inoculated with Sev-GFP or Sev-TauP301S.

Figure 19:
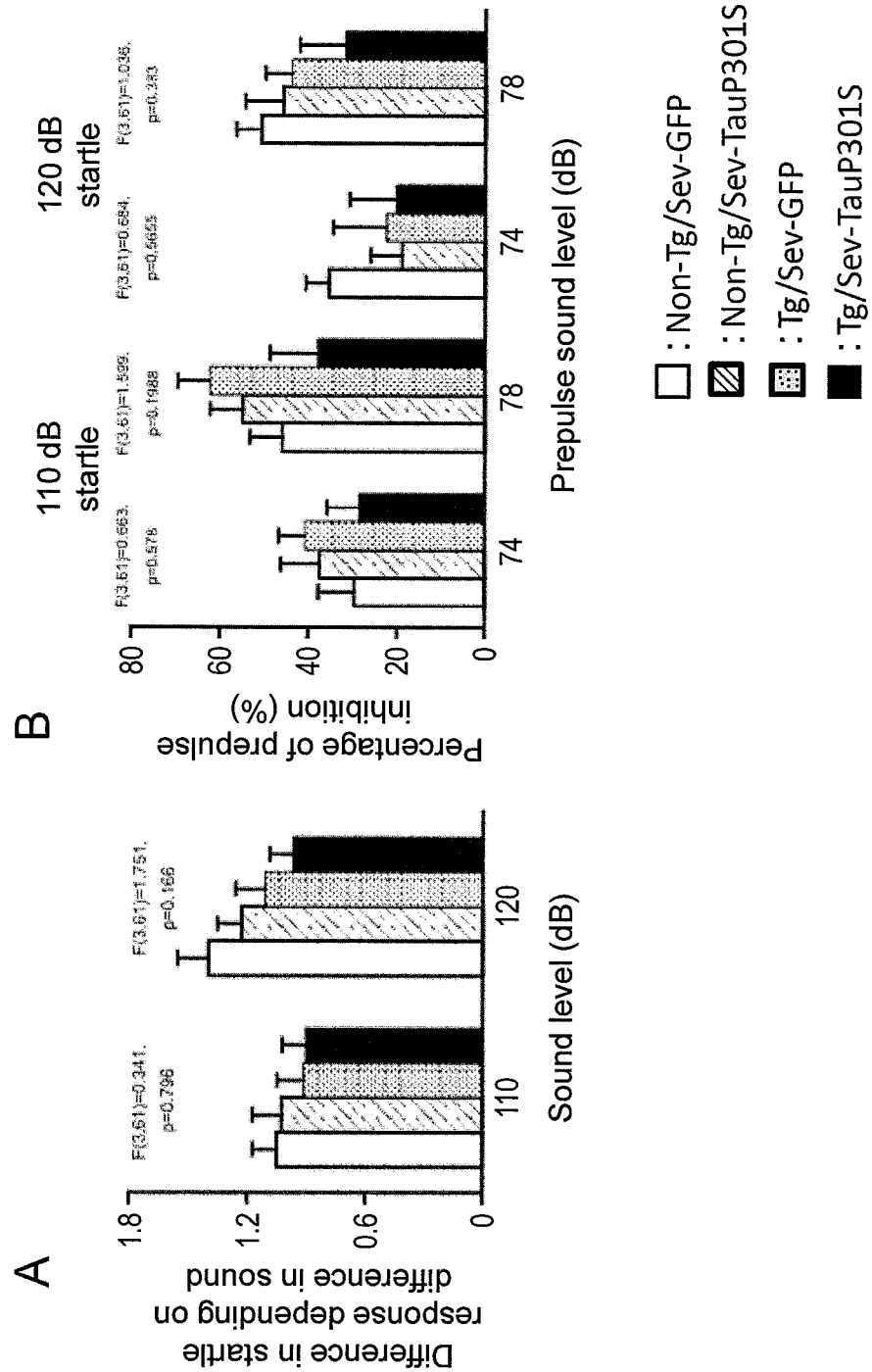

FIG. 19 is a pair of graphs showing the results of a prepulse inhibition test (startle responses (A) and effects of inhibiting the startle response by prepulses (B)) in wild-type mice and tauopathy model mice inoculated with Sev-GFP or Sev-TauP301S. Evaluation was performed by comparing effects of inhibiting the startle response of each mouse when caused to listen to a large sound after causing the mouse to listen to a weak sound in advance.

Figure 20:
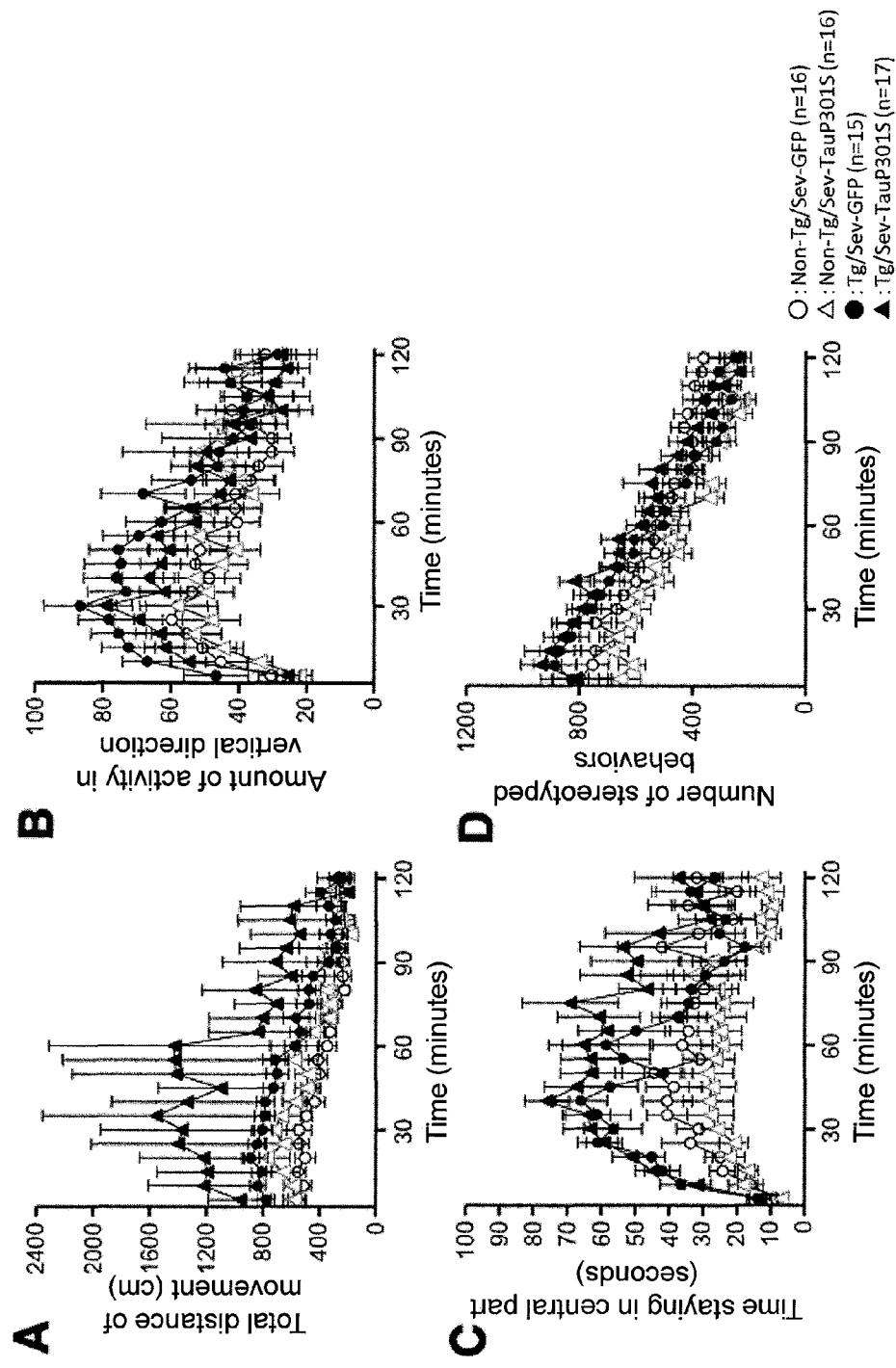

FIG. 20 is a series of graphs showing the results of an open field test in wild-type mice and tauopathy model mice inoculated with Sev-GFP or Sev-TauP301S. (A) shows the total distance of movement; (B), the amount of activity in the vertical direction; (C), the time staying in a central part; and (D), the number of stereotyped behaviors.

Figure 21:
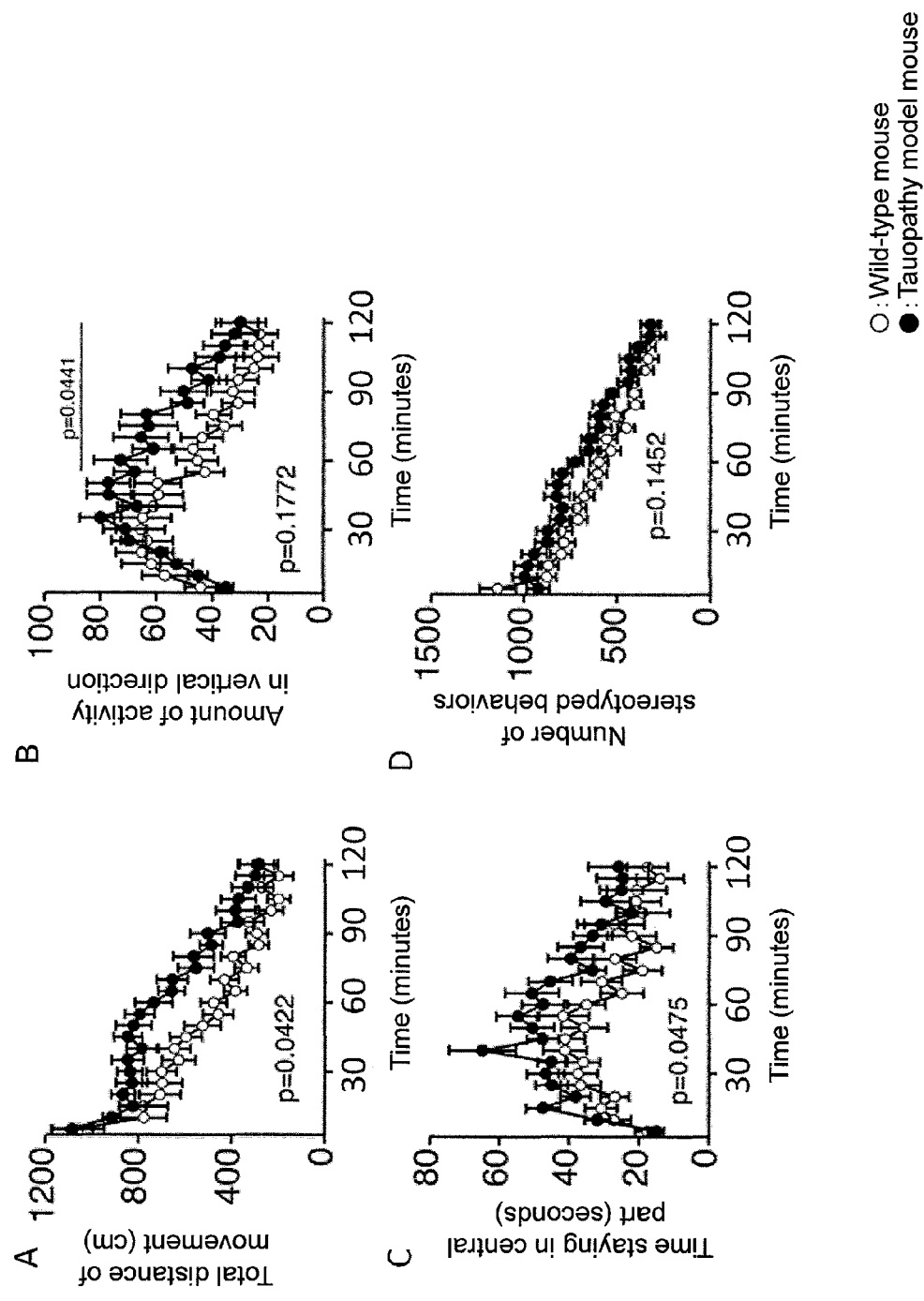

FIG. 21 is a series of graphs showing the results of an open field test in wild-type mice and tauopathy model mice. (A) shows the total distance of movement; (B), the amount of activity in the vertical direction; (C), the time staying in a central part; and (D), the number of stereotyped behaviors.

Figure 22:
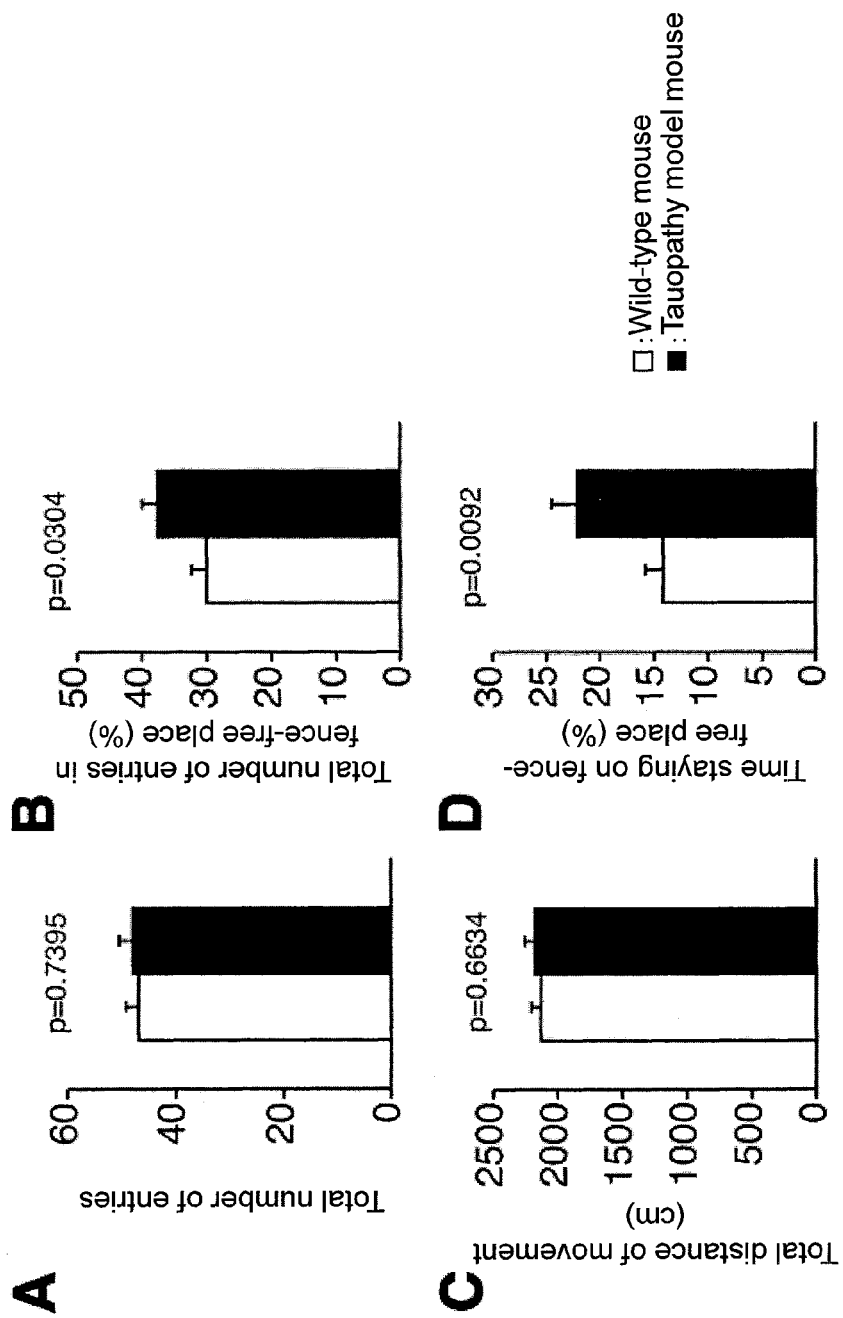

FIG. 22 is a series of graphs showing the results of an elevated plus maze test in wild-type mice and tauopathy model mice. (A) shows the number of entries into the open arms; (B), the percentage of entries into the open arms; (C), the distance of movement; and (D), the time staying on the open arms.

Figure 23:
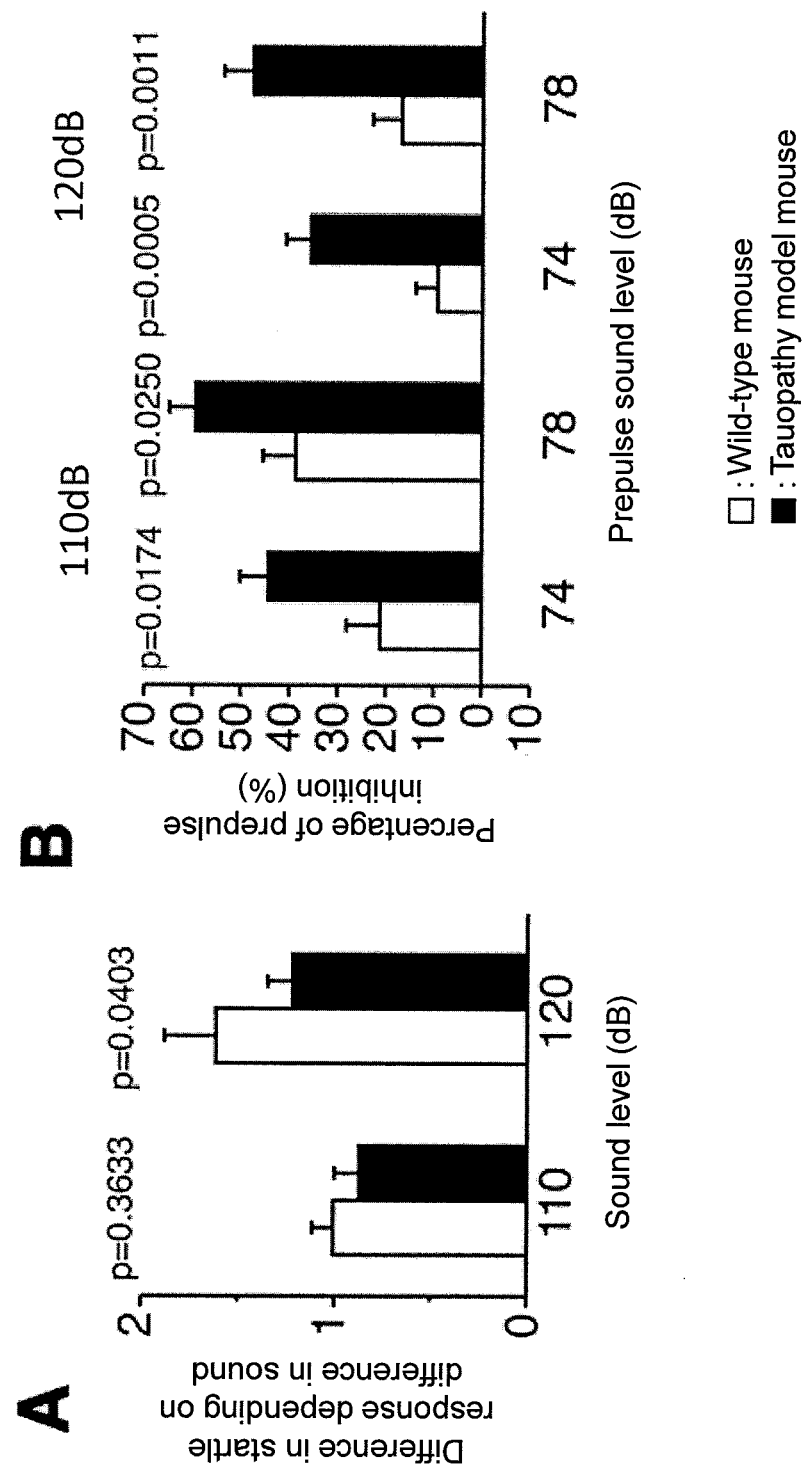

FIG. 23 is a pair of graphs showing the results of a prepulse inhibition test in wild-type mice and tauopathy model mice. (A) shows the difference in a startle response depending on the difference in a sound and (B) shows the percentage of prepulse inhibition (the percentage of the presence of the effect of inhibiting a startle response when a large sound was emitted after emitting a small sound in advance).

Figure 24:
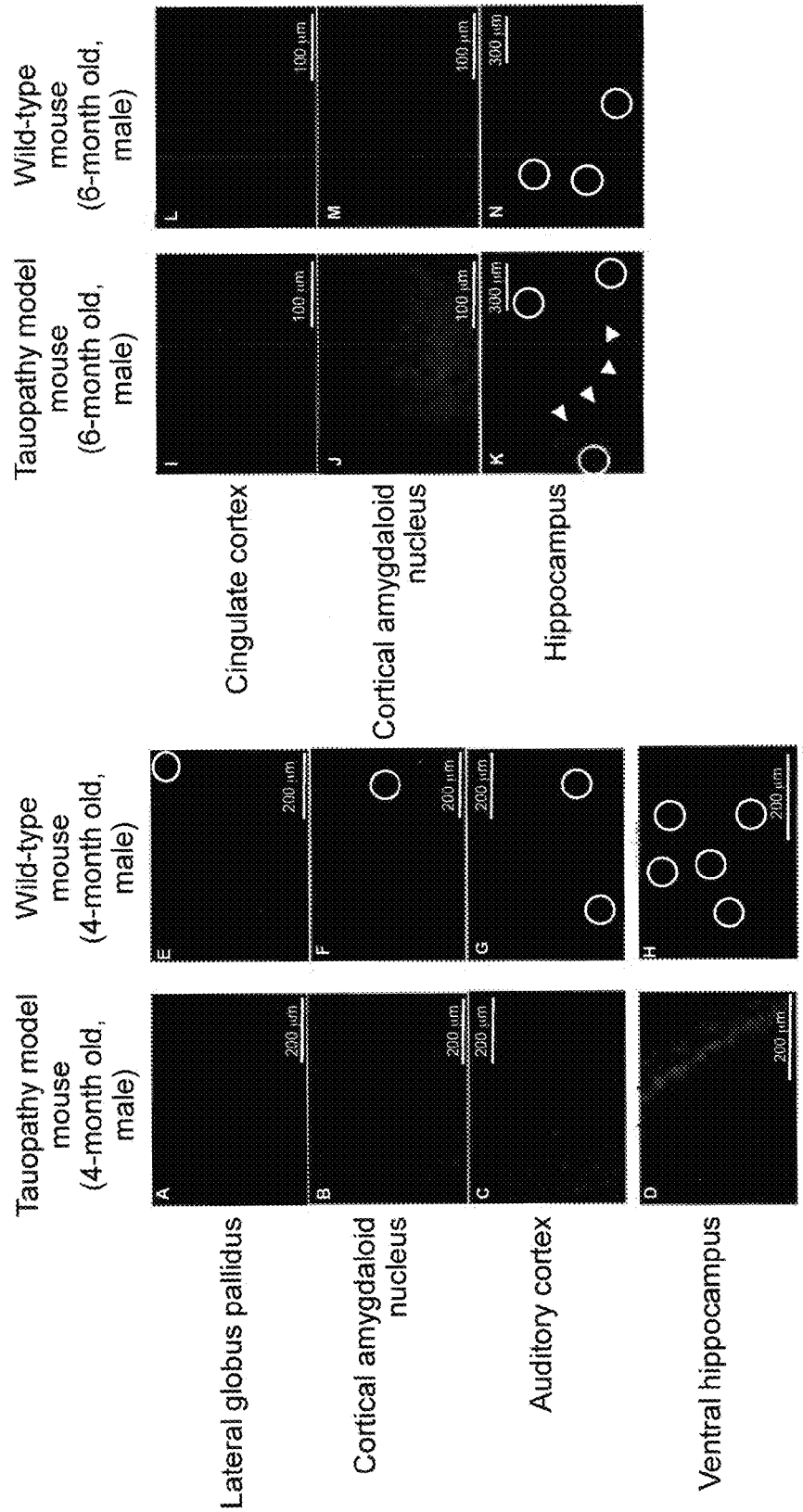

FIG. 24 is a series of photographs showing the results of analysis in 4-month old tauopathy model mice ((A) to (D)) and 4-month old wild-type mice ((E) to (H)), ((A), (E): lateral globus pallidus, (B), (F): cortical amygdaloid nucleus, (C), (G): auditory cortex, and (CA3; D, H): ventral hippocampus) and in 6-month old mice after behavioral analysis, ((I, L): cingulate cortex, (J, M): cortical amygdaloid nucleus, and (CA3; K, N): hippocampus).

The red stained portions indicate phosphorylated tau and the blue stained portions indicate cellular nuclei.

The arrow heads indicate the accumulation of phosphorylated tau protein and the circles indicate the non-specific reaction of an anti-mouse IgG antibody against the blood vessel.

Figure 25:
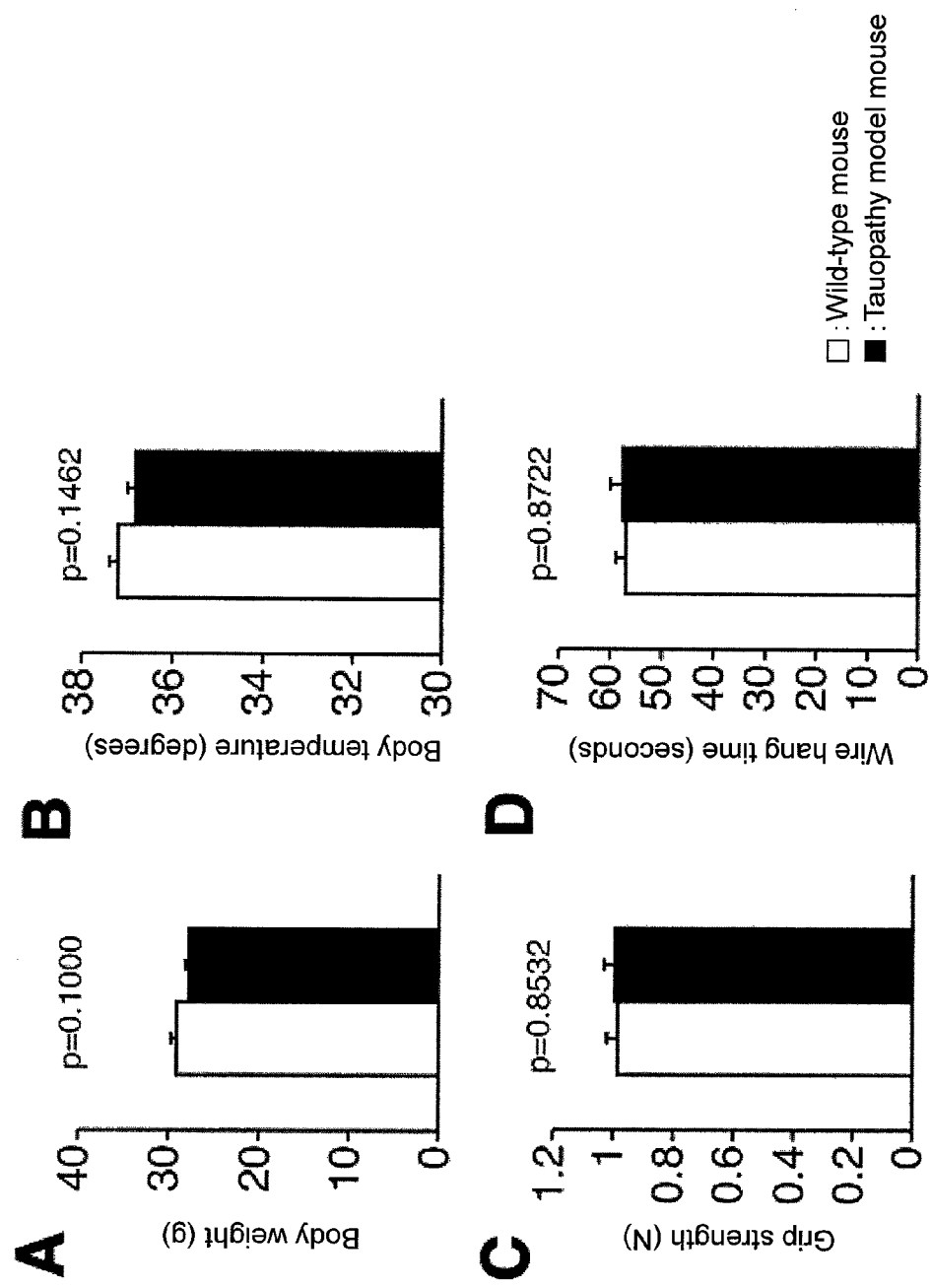

FIG. 25 is a series of graphs showing the results of general body measurements in 13-week old wild-type mice and tauopathy model mice. (A) shows body weight; (B), rectal temperature; (C), grip strength; and (D), the results of a wire hang test.

Figure 26:
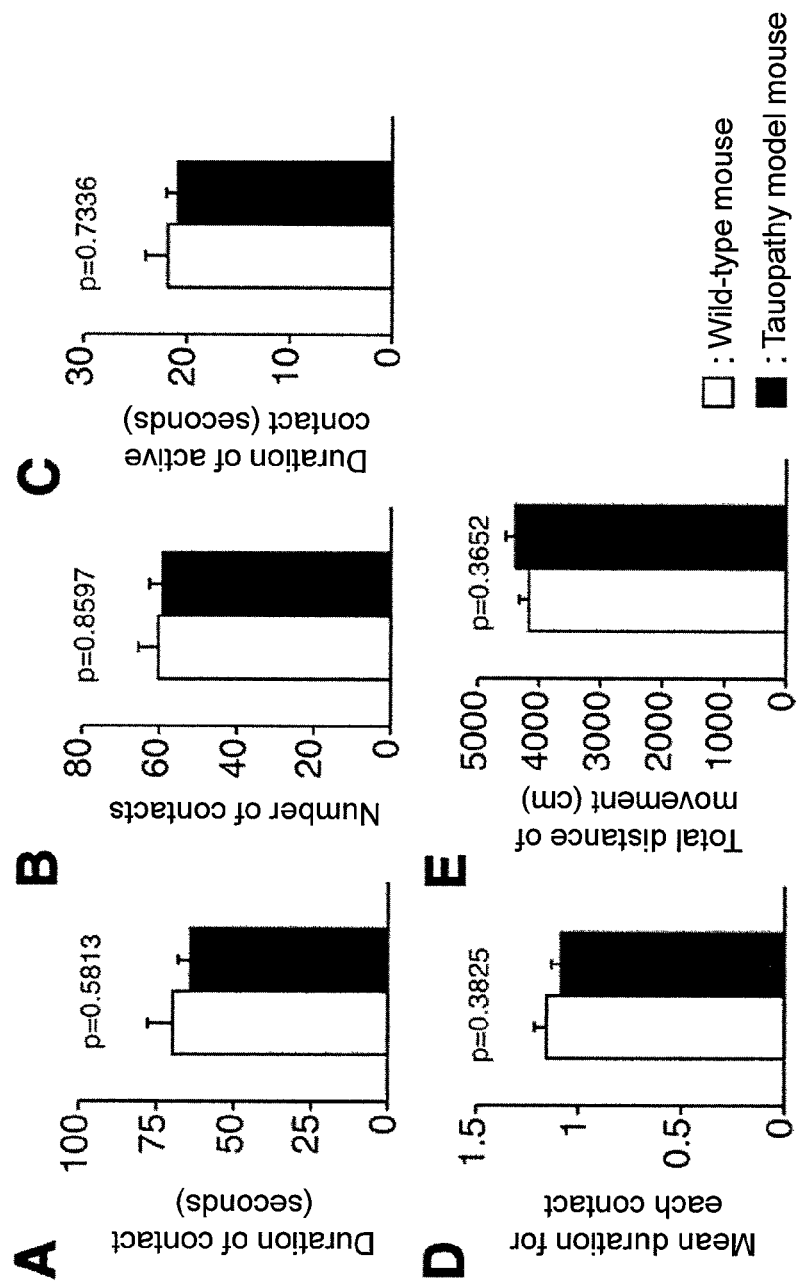

FIG. 26 is a series of graphs showing the results of a social interaction test. (A) shows the duration of contact; (B), the number of contacts; (C), the duration of active contact; (D), the mean duration for each contact; and (E), the total distance of movement during the test.

Figure 27:
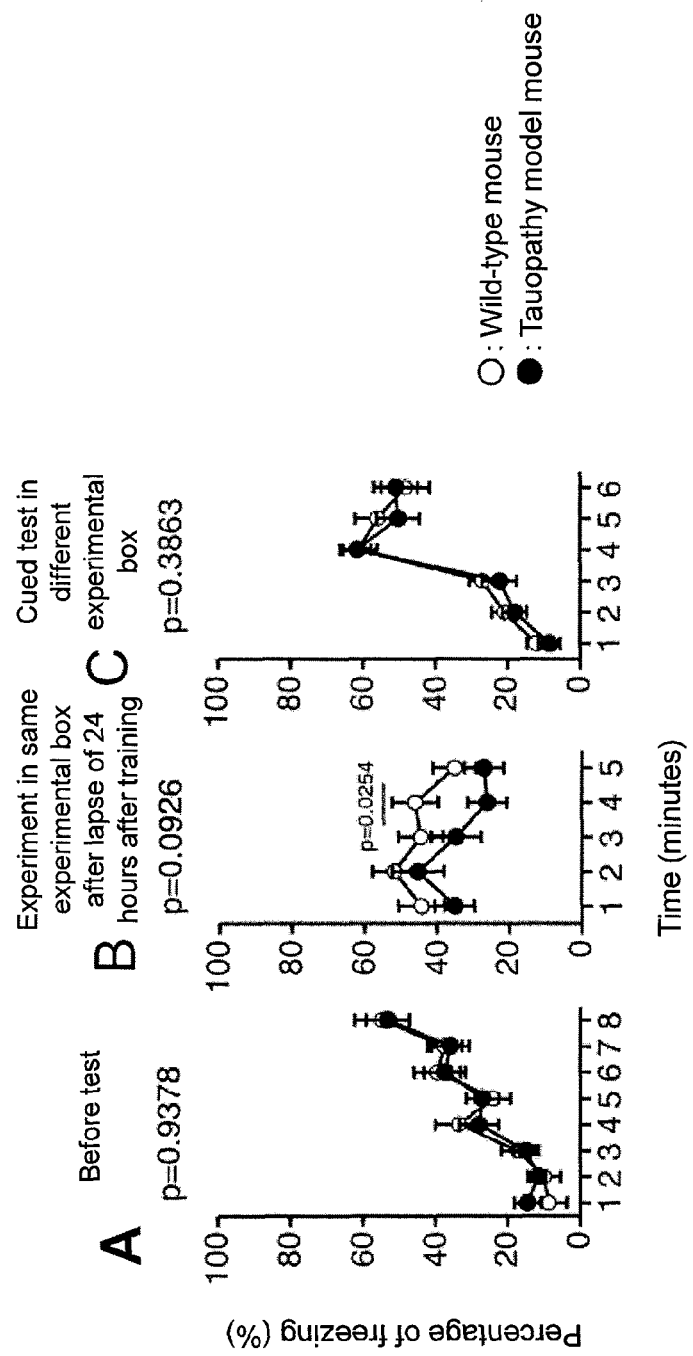

FIG. 27 is a series of graphs showing the results of a conditioned fear test (contextual learning) in wild-type mice and tauopathy model mice.

Figure 28:
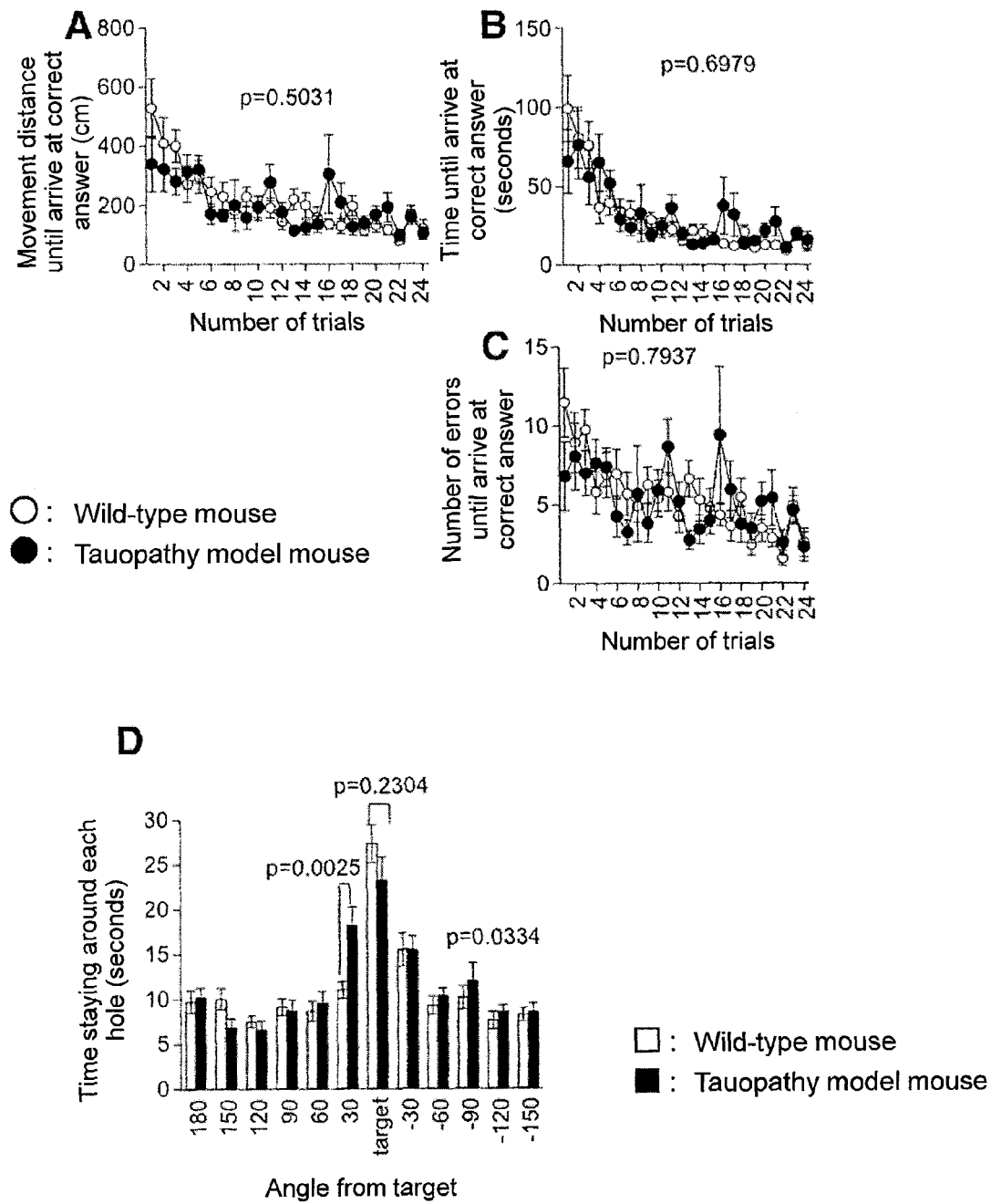

FIG. 28 is a series of graphs showing the results of a Barnes maze test (spacial memory) in wild-type mice and tauopathy model mice. (A) to (C) show the analysis results during the period of training, and (D) shows the results of a probe test after training.

MODES FOR CARRYING OUT INVENTION

The present invention will be described in further detail.

The present invention is characterized by use of a vector, as a vaccine, comprising a nucleic acid encoding a mutant tau protein as an active ingredient for preventing or treating tauopathy.

As used herein, "tauopathy" refers to a group of diseases in which phosphorylated tau protein is abnormally accumulated in the central nervous system and which are associated with nervous disorders (nerve degeneration and the like).

As used herein, "nucleic acid" means DNA or RNA.

As used herein, "subject" means a mammal, preferably a primate, more preferably a human.

<Mutant Tau Protein>

The tau protein is one of microtubule-associated binding proteins, also referred to as MAPT (microtubule-associated protein tau), has 6 isoforms produced by alternative splicing of tau gene, and is classified into 3-repeat type tau and 4-repeat type tau by the number of repeats of the C-terminal microtuble-binding site thereof (Hiroko Saito, Rinsho Kensa (Clinical Examination), 50 (10): 1121-1129 (2006) (Japan)). Human MAPT is present on the chromosome 17 (NG_007398.1), and for example, its transcript variants 1 to 6 are registered in GenBank (USA) under the accession numbers NM_016835.3, NM_005910.4, NM_016834.3, NM_016841.3, NM_001123067.2, and NM_001123066.2, respectively. The tau protein may be 3-repeat type tau or 4-repeat type tau, and especially 4-repeat type tau is known to be an isoform most often expressed in the human brain. The "tau protein" is preferably human tau protein.

The mutant tau protein of the present invention comprises the mutation of an amino acid residue at a position corresponding to at least one position selected from the group consisting of positions 257, 260, 266, 272, 279, 280, 284, 296, 301, 303, 305, 315, 317, 320, 335, 336, 337, 342, 352, 369, 389, and 406 of SEQ ID NO: 1 (NM_005910.4; isoform 2N4R) in the amino acid sequence of tau protein. The mutated position is preferably a position corresponding to position 257, 260, 272, 279, 296, 301, 303, 305, 335, 337, 342, 369, 389, or 406 of SEQ ID NO: 1 in the amino acid sequence of tau protein, and the more preferable mutated position is a position corresponding to at least position 301 of SEQ ID NO: 1 in the amino acid sequence of tau protein. This means that the mutated position may be only a position corresponding to position 301 of SEQ ID NO:1 or may comprise an amino acid residue at a position corresponding to at least one position selected from the above-specified group consisting of 257, 260, 266, 272, 279, 280, 284, 296, 303, 305, 315, 317, 320, 335, 336, 337, 342, 352, 369, 389, and 406 of SEQ ID NO: 1 in addition to at a position corresponding to position 301 of SEQ ID NO: 1.

The above mutation is substitution or deletion. The substitution is a mutation for which the amino acid residue at any of the above positions of tau protein is substituted by another amino acid residue, preferably an amino acid residue seen in a natural mutant, and examples of the substitution include the amino acid substitution of K257T, I260V, L266V, G272V, N279K, L284L, N296H, P301L, P301S, G303V, S305N, L315R, K317M, S320F, G335S, G335V, Q336R, V337M, E342V, S352L, K369I, G389R, or R406W in the amino acid sequence of SEQ ID NO: 1. The deletion is a deletion as seen in a natural mutant, for example, the deletion of K at position 280 or N at position 296 of SEQ ID NO: 1. According to the present invention, the mutation consists of mutation at one or more (for example, several (e.g., an integer of 2 to 10)) of the above positions.

According to the present invention, the mutation is preferably the substitution of an amino acid residue at the above-described position 301, for example, the amino acid substitution of P301S, P301L, or P301T.

As used herein, the description for the amino acid substitution, for example, "P301 S" means that the proline residue (P) at position 301 of the amino acid sequence of SEQ ID NO: 1 is substituted by a serine residue (S).

The mutation at position 301 is known to be associated, for example, with the fact that the age of onset of patients with frontotemporal dementia is relatively young and the disease rapidly progresses after onset (Sperfeld A D et al, Ann Neurol. 1999 November; 46 (5): 708-715; Yasuda M et al., Neurology, 55: 1224-1227, 2000); thus, the mutation at position 301 is important as a target for treating or preventing a tauopathy occurring at a young age and rapidly progressing (once developed) ascribed to the mutation at position 301, and the vaccine of the present invention is effective against such tauopathies.

<Vector>

The vector of the present invention comprises a nucleic acid encoding the above-described mutant tau protein. A secretory signal sequence is linked N-terminal to the mutant tau protein, resulting in that the nucleic acid is expressed by the vector incorporated into a cell and translated into a mutant tau protein precursor using an intracellular translation mechanism, which is then transferred to the cell membrane, and the signal sequence is cleaved by a signal peptidase to extracellularly secrete the mutant tau protein.

The DNA encoding the mutant tau protein linked to the secretory signal sequence can be synthesized using a conventional gene recombination technique. Such a technique is described, for example, in J. Sambrook et al., Molecular Cloning: A Laboratory Manual, 2nd Ed., Cold Spring Harbor Laboratory Press (1989) or F. M. Ausubel et al., Short Protocols in Molecular Biology, 5th Ed., John Wiley & Sons (2002).

The DNA encoding the mutant tau protein can be prepared, for example, by synthesizing cDNA from mRNA encoded by tau protein gene using a reverse transcriptase, incorporating the cDNA in a suitable plasmid vector, performing polymerase chain reaction (PCR) using the resultant vector as a template and primers into which a desired mutation is introduced to amplify a tau protein-coding sequence portion containing the mutation, obtaining a fragment containing the sequence portion by treatment with a restriction enzyme, incorporating the fragment in the plasmid vector treated with the same restriction enzyme, and then similarly performing PCR using the resultant vector as a template and primers enabling the amplification of the full-length tau protein-coding sequence for amplification.

The PCR comprises performing about 20 to 45 cycles of 3 steps consisting of denaturation, annealing, and amplification. The denaturation is a step of converting double stranded DNA into single stranded one and performed by heat treatment at a temperature of 92 to 98° C. for about 30 seconds to 2 minutes. The annealing is a step of binding the single stranded DNA to primers and performed by treatment at a temperature of 50 to 65° C. for about 10 seconds to 60 seconds. The amplification is a step of synthesizing a complementary strand using the single stranded DNA bound by the primers as a template and is performed by treatment at a temperature of about 72° C. for about 10 seconds to 7 minutes. Heat treatment may be carried out at about 94° C. for about 30 seconds to 5 minutes before starting the cycles, and amplification reaction can be performed at about 72° C. for about 1 minute to 10 minutes after the end of the cycles. The reaction is carried out using a PCR buffer, dNTPs (N=A, T, C, and G), and a thermostable DNA polymerase. The thermostable DNA polymerase may use a commercially available polymerase such as Taq Polymerase or Pfu Polymerase. It is convenient to use a commercially available PCR device (Takara Shuzo, Applied Biosystems, Perkin-Elmer, Bio-Rad, or the like) such as Thermocycler for automatically performing PCR.

The secretory signal sequence is any signal sequence cleavable by a signal peptidase present in human cells. Such a signal sequence encompasses a cell-specific one. Non-limiting examples of the secretory signal sequence include DNA encoding the signal sequence of amyloid precursor protein (APP) (NT_011512.11, NW_001838706.1, NM_201414.1, NM_201413.1, NM_000484.2, NM_001136130.1, NM_001136129.1): 5'-ggtctaga atgctgcccggtttggcactgctcctgctggccgcctggacggctcgggcgctt-3' (SEQ ID NO: 2) (where the actual APP signal sequence starts with the initiation codon atg (underlined) and the sequence tctaga 5' thereto is an restriction enzyme site) and DNA encoding the signal sequence of CD59 (NM_001127227.1, NM_001127226.1, NM_000611.5, NM_203331.2, NM_001127225.1, NM_203329.2, NM_203330.2, NM_001127223.1): 5'-atgggaatccaaggagggtctgtcctgt-tcgggctgctgctcgtcctggctgtcttctgccattcaggtcatagc-3' (SEQ ID NO: 3).

The DNA encoding a secretory signal sequence and the DNA encoding a mutant tau protein are ligated to each other in the order from 5'; PCR amplification is performed using the ligate as a template; and the resultant product is digested with a suitable restriction enzyme and then subcloned into a plasmid vector.

The plasmid vector usable in the above method may be any cloning vector. Non-limiting examples of such a vector include pBluescript-, pUC-, pBR-, and pET-series vectors.

The vector for bearing a nucleic acid encoding a mutant tau protein linked to a secretory signal obtained as described above may be any vector provided that it enables the expression of the nucleic acid in mammal cells such as human cells, and, for example, encompasses a plasmid or a virus vector for gene therapy.

Non-limiting examples of the plasmid for gene therapy include pBK-CMV, pcDNA3.1, and pZeoSV (Invitrogen and Stratagene) and pCAGGS (Gene Bridges).

Non-limiting examples of the virus vector for gene therapy include Sendai virus (SeV) vectors, adenovirus vectors, adeno-associated virus vectors, lentivirus vectors, herpes simplex virus vectors, replication-defective retrovirus vectors, measles virus vectors, rabies virus vectors, influenza virus vectors, respiratory syncytial virus (RSV) vectors, vesicular stomatitis virus (VSV) vectors, vaccinia virus vectors, and Sindbis virus vectors. Highly safe vectors such as replication-defective types thereof are preferable.

All of the above vectors may be used in the present invention; however, a vector which can be preferably used is a plasmid vector, a Sendai virus vector, an adenovirus vector, an adeno-associated vector, or a lentivirus vector, and a particularly preferable virus vector is a Sendai virus vector.

A promoter operable in eukaryote cells necessary for the expression of foreign DNA, for example, each of promoters such as CMV IE, dectin-1, dectin-2, human CD11c, F4/80, and MHC class II may be inserted into the vector. In addition to this element, regulatory sequences such as an enhancer, a replication origin, a ribosomal binding site, a terminator, and a polyadenylation site and selection markers such as a drug resistance gene can be contained in the vector.

The vector may also be any vector enabling a desired nucleic acid to be constantly, autonomously, or inducibly expressed; however, it is preferably a vector causing the desired nucleic acid to be autonomously expressed in terms of safety.

The Sendai virus vector has a relatively high gene expression rate and also has a high safety with no carcinogenic risk due to a chromosomal insertion mutation. This vector does not enter the cellular nucleus, replicates in the cytoplasm, and enables the expression of a foreign protein at a high level.

It is known that the genes involved in autonomous replication in a Sendai virus are NP, P/C, and L genes and the genes responsible for transmissibility are M, F, and HN genes. When this virus is used as a vector, it may be provided with the above genes, or may lack some of the genes, for example, F gene, M gene, and HN gene (Protein, Nucleic Acid and Enzyme, 51: 27-37, 2006). High safety is secured particularly by the deletion of the gene of F protein as a membrane fusion protein involved in invasion into host cells (JP Patent Publication (Kokai) No. 2009-268471 A, JP Patent Publication (Kohyo) No. 2008-536476, and WO 00/70070).

The nucleotide sequences of the above genes of the Sendai virus are registered in GenBank and the like as follows (JP Patent Publication (Kohyo) No. 2008-536476):

for the NP gene, M29343, M30202, M30203, M30204, M51331, M55565, M69046, X17218, and the like;

for the P gene, M30202, M30203, M30204, M55565, M69046, X00583, X17007, X17008, and the like;

for the L gene, D00053, M30202, M30203, M30204, M69040, X00587, X58886, and the like;

for the M gene, D11446, K02742, M30202, M30203, M30204, M69046, U31956, X00584, X53056, and the like;

for the F gene, D00152, D11446, D17334, D17335, M30202, M30203, M30204, M69046, X00152, X02131, and the like; and for the HN gene, D26475, M12397, M30202, M30203, M30204, M69046, X00586, X02808, X56131, and the like.

The Sendai virus genome cDNA can be constructed according to a method as described, for example, in Yu, D. et al., Genes Cells 2: 457-466, 1997, or Hasan, M. K. et al., J. Gen. Virol. 78: 2813-2820, 1997. In addition, the reconstruction of the virus from the cDNA can be carried out according to a method as described in WO 97/16539; WO 97/16538; WO 00/70055; WO 00/70070; WO 01/18223; WO 03/025570; JP Patent Publication (Kohyo) No. 2008-536476; Tokusumi, T. et al., Virus Res. 86: 33-38 (2002); Li, H. et al., J. Virol. 74: 6564-6569 (2000); or the like. As host cells usable for the reconstruction of a virus vector, there are known, for example, cultured cells such as simian kidney-derived LLC-MK2 cells (ATCC CCL-7) and CV-1 cells (e.g., ATCC CCL-70) and hamster kidney-derived BHK cells (e.g., ATCC CCL-10), and human-derived 293T cells; further, to obtain a large amount of a virus vector, the virus vector obtained from the above host cells can be infected and proliferated in an embryonated egg and then purified (JP Patent Publication (Kohyo) No. 2008-536476, WO 00/70055, and WO 00/70070). The titer of the recovered virus can be determined, for example, by measuring CIU (Cell-Infectious Unit) or hemagglutination activity (HA) (WO 00/70070).

The reconstitution of an F gene-deleted Sendai virus vector can also be carried out according to the method described in WO 00/70055, WO 00/70070, JP Patent Publication (Kohyo) No. 2008-536476, or the like. Here, a helper cell line expressing Sendai virus F protein is established, and this is used to recover infecting virus particles from the F gene-deleted genome.

According to Examples to be described later, using examples from the above methods, cDNA of an F gene-deleted Sendai virus vector (Z strain) is digested with a restriction enzyme NotI, and a linked fragment of a secretory signal sequence (e.g., APP signal sequence or CD59 signal sequence) and a mutant tau protein (TAU (P301 S)) is inserted into the noncoding region between the transcription initiation region and the coding region (ORF) of Sendai virus nucleocapsid (NP) protein gene to construct a mutant tau gene-bearing F gene-deleted Sendai virus vector (Sev-TauP301S). The actually constructed plasmid for reconstituting the Sendai virus vector is pcDNA3-APP-TauP301S (FIG. 14); the initiation codon (atg) is bound to the 5' terminal end of the secretory signal sequence, and the consensus sequence of Kozak (e.g., gccacc or ccacc) may be further linked ahead of the initiation codon. For the reconstitution of the vector, a helper cell line expressing Sendai virus F protein is used (WO 00/70070).

For the adenovirus vector, an E1 region-deleted adenovirus vector may be used. An E3 region may be deleted in addition to the E1 region; however, the deletion of the E3 region is not always essential. The adenovirus vector is described, for example, in JP Patent Publication (Kokai) Nos. 2008-017849 and 2000-166581; JP Patent Publication (Kohyo) No. 2003-518915; Hitt, M. et al., "Construction and propagation of human adenovirus vectors" In Cell Biology: A Laboratory Handbook (Celis, J. E. ed.), Third Ed., Vol. 1, Academic Press (2005), or Hitt, M. et al., "Techniques for human adenovirus vector construction and characterization" In Methods in Molecular Genetics (Adolph, K. W. ed.), Vol. 7, Academic Press (1995).

For other virus vectors, vectors improved for use in gene therapy are described in the literature and can be used for the present invention.

<Vaccine>

The vaccine of the present invention can be used for preventing or treating tauopathy. The vaccine can induce an antibody to (optionally phosphorylated) tau protein in a subject in a further sustained manner compared with a case where a mutant tau protein is administered directly (see FIGS. 4 and 6).

The vaccine of the present invention activates microglia in the brain of a subject, which thereby phagocytizes a mutant tau protein. The clearance of the mutant tau protein as a causative agent for tauopathy by microglia inhibits the accumulation of the protein and suppresses the progression of the symptoms of tauopathy.

An in vivo test using tauopathy model mice (P301S Tau transgenic mice) showed that the vaccine of the present invention had the effect of improving tauopathy, especially tauopathy dementia. In other words, the reduced recent memory and the unsociability observed in dementia were improved by the inoculation of the vaccine of the present invention, whereas the improving effect was not observed when a recombinant mutant tau protein was inoculated; thus, the superiority of the vaccine of the present invention was demonstrated. The vaccine of the present invention was also observed to have the effect of improving the hyperactivity (restlessness) often observed in dementia, like the recombinant mutant tau protein. Thus, the vaccine of the present invention has the effect of improving the reduced recent memory and/or the abnormal social interaction and/or the abnormal anxiety-like behavior and/or the impaired memory observed in dementia.

Because of having the above effects, the vaccine of the present invention can be used for preventing or treating tauopathy, especially diseases such as Alzheimer disease, FTDP-17 (frontotemporal dementia accompanied by parkinsonism associated with chromosome 17), Down syndrome, Pick disease, parkinsonism-dementia complex, neurofibrillary tangle-predominant form of dementia, dementia pugilistica, progressive supranuclear palsy, argyrophilic grain dementia, corticobasal degeneration, postencephalitic parkinsonism, subacute sclerosing panencephalitis, myotonic dystrophy, Fukuyama type muscular dystrophy, Guam amyotrophic lateral sclerosis-parkinsonism complex, and amyotrophic lateral sclerosis accompanied by neurofibrillary tangle in the Kii peninsula.

The vaccine of the present invention may contain pharmaceutically acceptable carriers and additives such as saline, Ringer's solution, a buffer, vegetable oil, a suspending agent, a surfactant, a stabilizer, and a preservative, if necessary. An adjuvant for increasing immunogenicity may be added to the vaccine. Examples of the adjuvant include immunostimulants such as aluminum salts (alum), saponins, muramyl(di)peptides, cytokinse (IL-2, 4, 6, or the like), cholera toxins, and salmonella toxins.

The vaccine of the present invention may be inoculated by a route such as a subcutaneous, intradermal, intranasal, intramuscular, intravenous, or intraperitoneal route. A preferred preparation is an injection, an inhalant, or the like. The inhalant can be enclosed in an inhalation system enabling it to be inhaled by weighing the dose. The dosage should be properly determined depending on the symptoms, severity, age, sex, and body weight of a subject (a mammal, preferably a human); however, although the dosage can vary according to the form and administration method of the vaccine, non-limiting examples thereof include $10^4$ to $10^{14}$ pfu (plaque-forming units), preferably $10^5$ to $10^{13}$ pfu, more preferably $10^6$ to $10^{11}$ pfu, or $10^5$ to $10^9$ CIU (cell infection units) for the virus vector and about 1 µg to 500 µg for the plasmid vector; it may also be outside the above range provided that the vaccine effect is exerted in any case.

It is also possible to use a liposome in order to promote permeation through the cell membrane. The liposome is preferably a cationic liposome. The cationic liposome has been shown to mediate the intracellular delivery of plasmid DNA (Nature 337: 387 (1989)). The cationic liposome can also be bound to a membrane-permeable peptide to facilitate the intracellular delivery thereof. For the liposome, one may refer to the literature including: Brigham et al., Am. J. Med. Sci., 298: 278 (1989); Osaka et al., J. Pharm. Sci., 85(6): 612-618 (1996); San et al., Human Gene Therapy, 4: 781-788 (1993), Senior et al., Biochemica et Biophysica Acta, 1070: 173-179 (1991); Kabanov and Kabanov, Bioconjugate Chem. 1995; 6: 7-20; Remy et al., Bioconjugate Chem., 5: 647-654 (1994); Behr, J-P., Bioconjugate Chem., 5: 382-389 (1994); Wyman et al., Biochem., 36: 3008-3017 (1997).

EXAMPLES

The present invention will be described below in detail with reference to Examples. However, the scope of the invention is not to be limited to these Examples.

Example 1

Construction of Mutant Tau Gene-Bearing F Gene-Deleted Sendai Virus Vector

1) Construction of Sendai Virus Vector Expressing Secretory Signal Sequence and Tau Protein The secretory signal sequence used the following sequence, based on amyloid precursor protein (APP, Genbank accession number: NT_011512.11, NW_001838706.1, NM_201414.1, NM_201413.1, NM_000484.2, NM_001136130.1, and NM_001136129.1):

```
                                              (SEQ ID NO: 2)
5'-ggtctagaatgctgcccggtttggcactgctcctgctggccgcct
ggacggctcgggcgctt-3.
``` cDNA of a mutant tau protein (TauP301S) was amplified by PCR using the nucleotide sequence of a human 1N4R tau protein (Genbank accession number: NM_001123067.2), in which mutation is contained [mutation from the codon of proline (P) to the codon of serine (S) at position 272 of the amino acid sequence described in NM_001123067.2 (the position corresponding to position 301 of SEQ ID NO: 1); the serine codon (tcg) at positions 884 to 886 of SEQ ID NO: 13] as a template and employing the following primers:

```
5' Forward primer:
                                              (SEQ ID NO: 4)
gctgagccccgccaggag 3' Reverse primer:
                                              (SEQ ID NO: 5)
tcacaaaccctgcttggccag
```

APP secretory signal was bound to the cDNA of tau protein amplified by PCR, and the resultant was used as a template to perform PCR employing the following primers:

```
5' Forward primer:
                                              (SEQ ID NO: 6)
aaagaattcggcttggtctagaatgctgcccggtttggcac 3' Reverse primer:
                                              (SEQ ID NO: 7)
aaagaattctcacaaaccctgcttggccag
```

The resultant PCR product was digested with a restriction enzyme EcoRI and then subcloned into pcDNA3 (Invitrogen).

The construction of the mutant tau gene-bearing F gene-deleted Sendai virus vector was carried out according to a method as described in reports of Li et al. (Li H et al. J. Virology, 74: 6564-6569 (2000); WO 00/70070). cDNA of an F gene-deleted Sendai virus vector (Z strain) was digested with a restriction enzyme NotI, and a linked fragment of the secretory signal sequence and the mutant tau protein was inserted into the non-coding region between the transcription initiation sequence and the coding region of Sendai virus nucleocapsid (NP) protein gene to construct the mutant tau gene-bearing F gene-deleted Sendai virus vector.

An F gene-deleted Sendai virus vector expressing EGFP used as a control was also constructed using the EGFP portion of pTRES2-EGFP vector (Clonetech).

2) Reconstitution and Amplification of Mutant Tau Gene-Bearing F Gene-Deleted Sendai Virus Vector The reconstitution of the F gene-deleted Sendai virus vector was performed with reference to the reports of Li H et al. (Li H et al. J. Virology, 74: 6564-6569 (2000); WO 00/70070). Because the Sendai virus vector is of a F-gene deletion type, packaging cells expressing F protein were used to prepare the mutant tau gene-bearing F gene-deleted Sendai virus vector (hereinafter referred to as "Sev-TauP301S") and the EGFP gene-bearing F gene-deleted Sendai virus vector (hereinafter referred to as "Sev-GFP").

Example 2

Construction of Plasmid Vector Bearing Mutant Tau Gene

1) Construction of Plasmid Vector Expressing Secretory Signal Sequence and Tau Protein The secretory signal sequence used the following sequence among the nucleotide sequences of CD59 protein (Genbank accession number: NM_001127227.1, NM_001127226.1, NM_000611.5, NM_203331.2, NM_001127225.1, NM_203329.2, NM_203330.2, and NM_001127223.1):

```
                                        (SEQ ID NO: 3)
5'-atgggaatccaaggagggtctgtcctgttcgggctgctgctcgtc
ctggctgtcttctgccattcaggtcatagc-3'
``` cDNA of a mutant tau protein (TauP301S) was amplified by PCR using the sequence of a human 1N4R tau protein (Genbank accession number: NM_001123067.2), in which mutation is contained [mutation from the codon of proline (P) to the codon of serine (S) at position 272 of the amino acid sequence described in NM_001123067.2 (the position corresponding to position 301 of SEQ ID NO: 1); the serine codon (agt) at positions 898 to 900 of SEQ ID NO: 12] as a template and employing the following primers. The mutant tau carried by the plasmid vector was adapted to have a different serine codon sequence in order to differentiate from the mutant tau carried by the Sendai virus vector.

```
    5' Forward primer:
                                        (SEQ ID NO: 8)
    gctgagccccgccaggag 3' Reverse primer:
                                        (SEQ ID NO: 9)
    tcacaaaccctgcttggccag
```

The CD59 secretory signal was linked to the cDNA of tau protein amplified by PCR, which was then used as a template to perform PCR employing the following primers:

```
    5' Forward primer:
                                        (SEQ ID NO: 10)
    ttgaattcgccaccatgggaatccaaggag 3' Reverse primer:
                                        (SEQ ID NO: 11)
    aattctcgagtcacaaaccctgcttggc
```

The resultant PCR product was digested with restriction enzymes EcoRI and XhoI and inserted between the cleavage sites produced by digesting the multiple cloning site of pcDNA3.1(+) plasmid vector (Invitrogen) with restriction enzymes EcoRI and XhoI.

2) Amplification of Mutant Tau Gene-Bearing Plasmid Vector

The amplification of the plasmid vector was performed in the following manner on the basis of instructions for the product pcDNA3.1 issued by Invitrogen. *Escherichia coli* strain DH5α was transformed with the plasmid vector. The resultant was then seeded on an LB-ampicillin medium, and small-volume culture was performed for each single clone for purification. The plasmid was extracted using Nucleobond Plasmid Purification Kit (MACHEREY-NAGEL), and sequenced to confirm whether it is correctly replicated, and thereby an effective clone was selected. The amplification of the plasmid vector for inoculation into mice was performed by the large scale culture of the selected clone, and the extraction of the plasmid used Nucleobond Plasmid Purification Kit of endotoxin-free grade.

Example 3

In Vivo Test Using Mutant Tau Gene-Bearing F Gene-Deleted Sendai Virus Vector

1) Nasal Administration of GFP-Expressing F Gene-Deleted Sendai Virus Vector to Mouse The GFP-bearing F gene-deleted Sendai virus vector of the present invention (hereinafter referred to as "Sev-GFP") was nasally administered to 3-month old tauopathy model mice (P301S Tau transgenic mice) (Yoshiyama, Y, et al. Neuron 53, 337-351 (2007); a gift from Dr. Trojanowski, University of Pennsylvania) to examine infection efficiency.

One week after administering Sev-GFP $5 \times 10^6$ CIU/animal, the expression of GFP in the nasal mucosa was analyzed by taking a fluorescent image and a light field image using a multi-purpose microscope (BZ-9000, Keyence).

Figure 1:
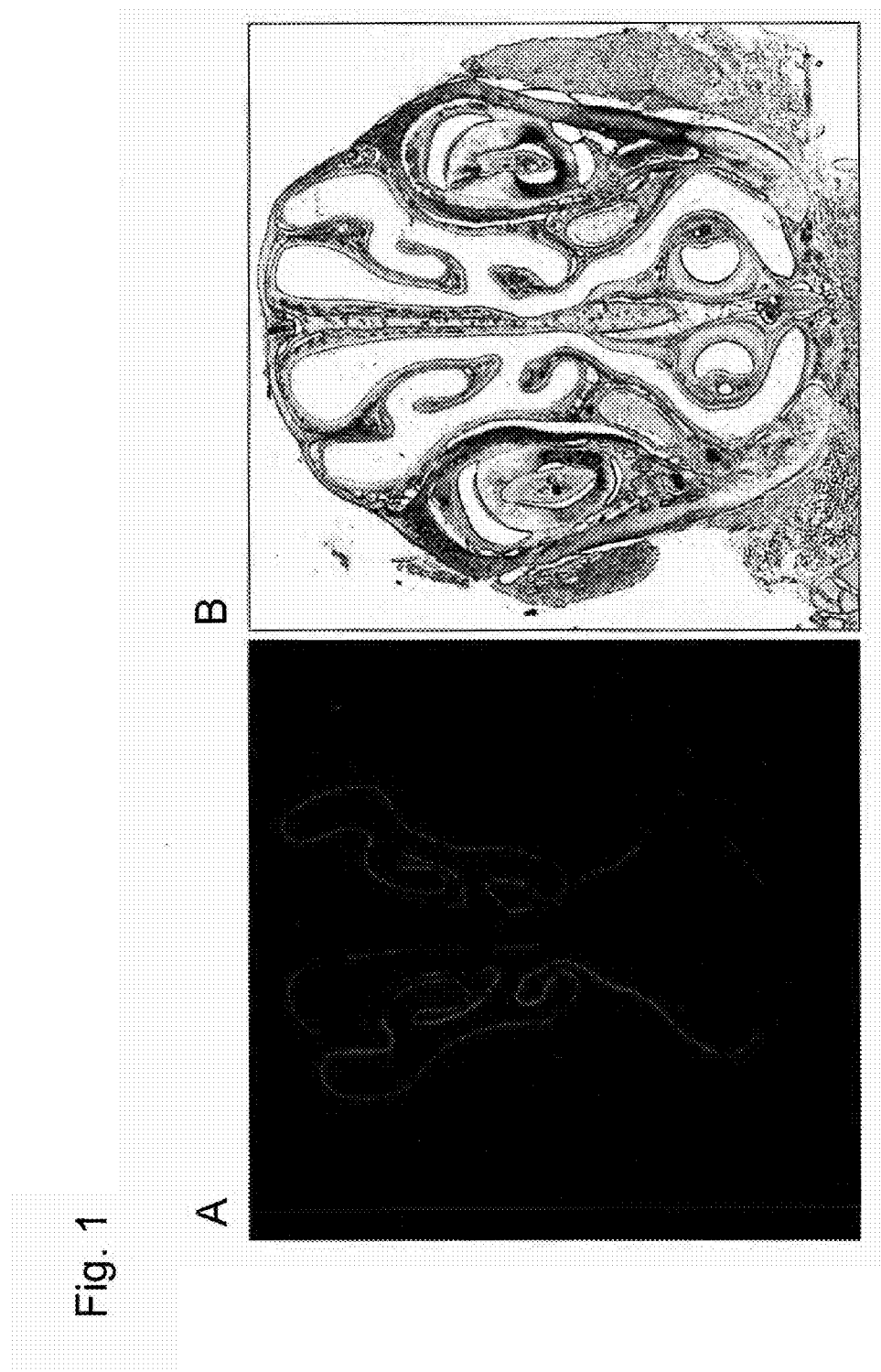
FIG. 1 is a pair of photographs showing the results of examining the efficiency of infection in a tauopathy model mouse to which a GFP-bearing F gene-deleted Sendai virus vector (Sev-GFP) was nasally administered (P301S Tau transgenic mouse). The expression of GFP in the brain of an Sev-GFP-inoculated mouse was analyzed by taking the fluorescent image (A) and the light field image (B) using a multi-purpose microscope (BZ-9000, Keyence).

As a result of analysis, the expression of GFP was observed in a large area of the nasal mucosa, confirming that the nasal administration of the Sendai virus vector was effective (FIG. 1).

2) Effect of Suppressing Phosphorylated Tau Protein Expression by Sev-TauP301S Inoculation (1)

Five months after nasal (intranasal) administration of Sev-TauP301S $5 \times 10^6$ CIU/animal to 3-month old tauopathy model mice, the mice were dissected and the tissue section of the hippocampal corona was prepared. Sev-GFP was used as a control vaccine. In the above two groups, inoculation was performed into 13 and 11 tauopathy model mice, respectively.

Figure 2:
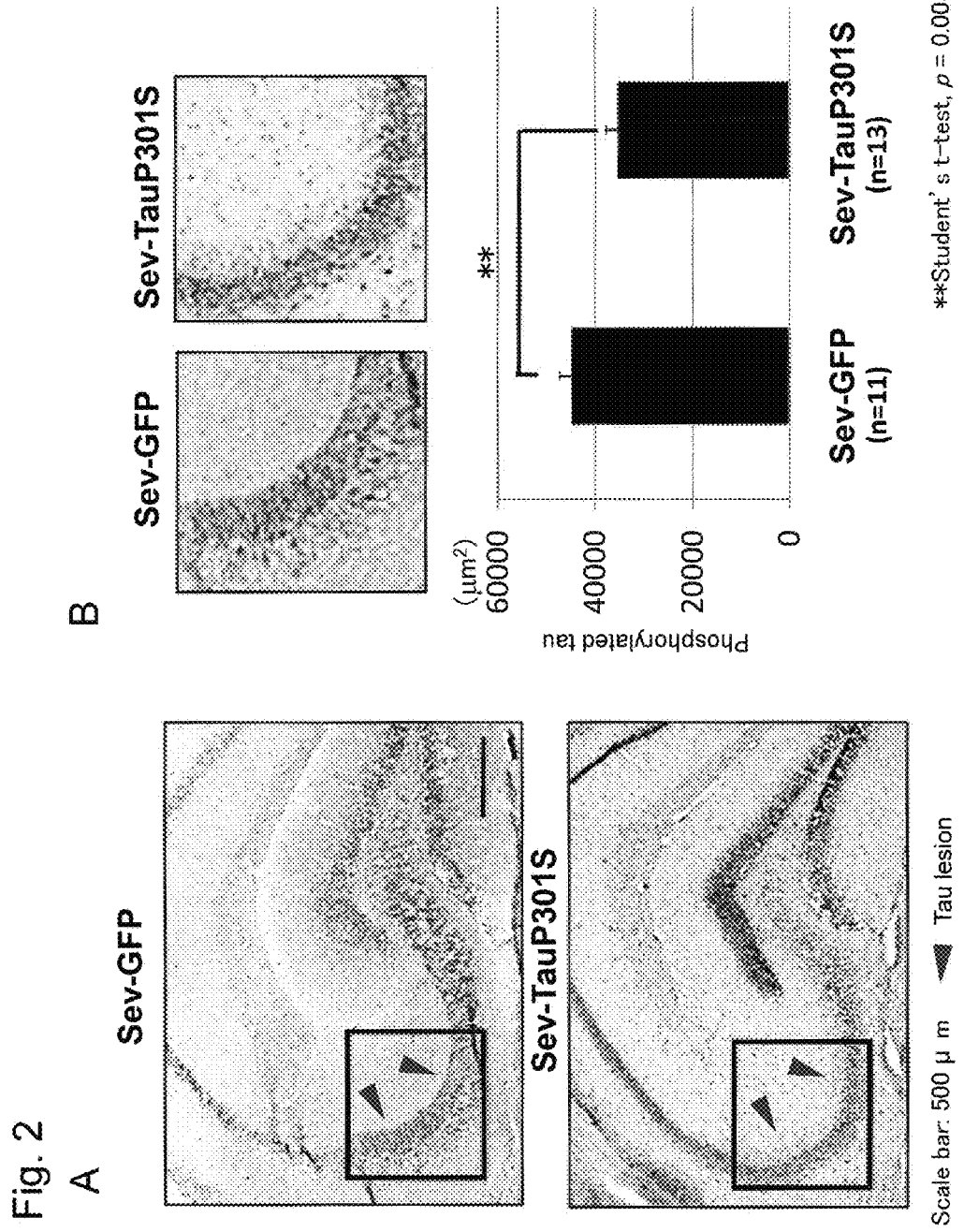
FIG. 2 is a series of photographs and a graph showing the results of inoculating tauopathy model mice with a tau protein-bearing F gene-deleted Sendai virus vector (Sev-TauP301S) to analyze its effect of suppressing the expression of phosphorylated tau protein. Sev-GFP (where GFP represents a nucleic acid encoding a green fluorescent protein) was used as a control. On the 5th month after inoculation, the hippocampal coronal section of each mouse was immunostained with an anti-phosphorylated tau protein antibody (ATB, Innogenetics). The arrow heads indicate tau lesions. After immunostaining, the area of the accumulation region in the hippocampal C3 region was measured using software provided with a multi-purpose microscope (BZ-9000, Keyence). The mean±standard error was calculated for each of the Sev-GFP-inoculated group and the Sev-TauP301S-inoculated group, and statistical analysis was performed by Student's t-test.

To measure the expression level of phosphorylated tau, the hippocampal tissue section was subjected to immunostaining. The mouse hippocampal coronal section was reacted with an anti-phosphorylated tau protein antibody (AT8, Innogenetics) and, after washing, subjected to immunostaining using a biotin-labeled horse anti-mouse IgG antibody (Vector) as a secondary antibody. After immunostaining, the area of the region of accumulation in the hippocampal CA3 region was measured using analysis software provided with a multipurpose microscope (BZ-9000, Keyence). The mean±standard error was calculated for each of the Sev-GFP group and the Sev-TauP301S group, and statistical analysis was performed by Student's t-test. As a result, the suppression of the expression of phosphorylated tau protein in the hippocampus was suggested in the Sev-TauP301S administered group compared to in the Sev-GFP group (FIG. 2).

3) Effect of Suppressing Phosphorylated Tau Protein Expression by Sev-TauP301S Inoculation (2)

The effect of suppressing the expression of tau protein by Sev-TauP301 S or Sev-GFP inoculation was analyzed by a western blott method using a hippocampus-derived protein.

The method using the western blott method is as follows. The hippocampal tissue was homogenized with RAB-HS buffer and then centrifuged at 4° C. and 50,000×g for 40 minutes, followed by treating the supernatant with SDS, and subjected to electrophoresis on SDS-PAGE applying 15 µg/sample. After electrophoresis, proteins on the gel were transferred to a PVDF membrane and reacted with an anti-phosphorylated tau protein antibody (AT8, Innogenetics), and then the membrane was washed, followed by performing chemiluminescent detection with ECL (GE Healthcare) using an HRP-labeled sheep anti-mouse IgG antibody (GE Healthcare) as a secondary antibody. After evaluating phosphorylated tau protein, the antibody was detached with Stripping solution (Nakalai), followed by again detecting it by the same method using an anti-β-actin antibody (SIGMA).

Figure 3:
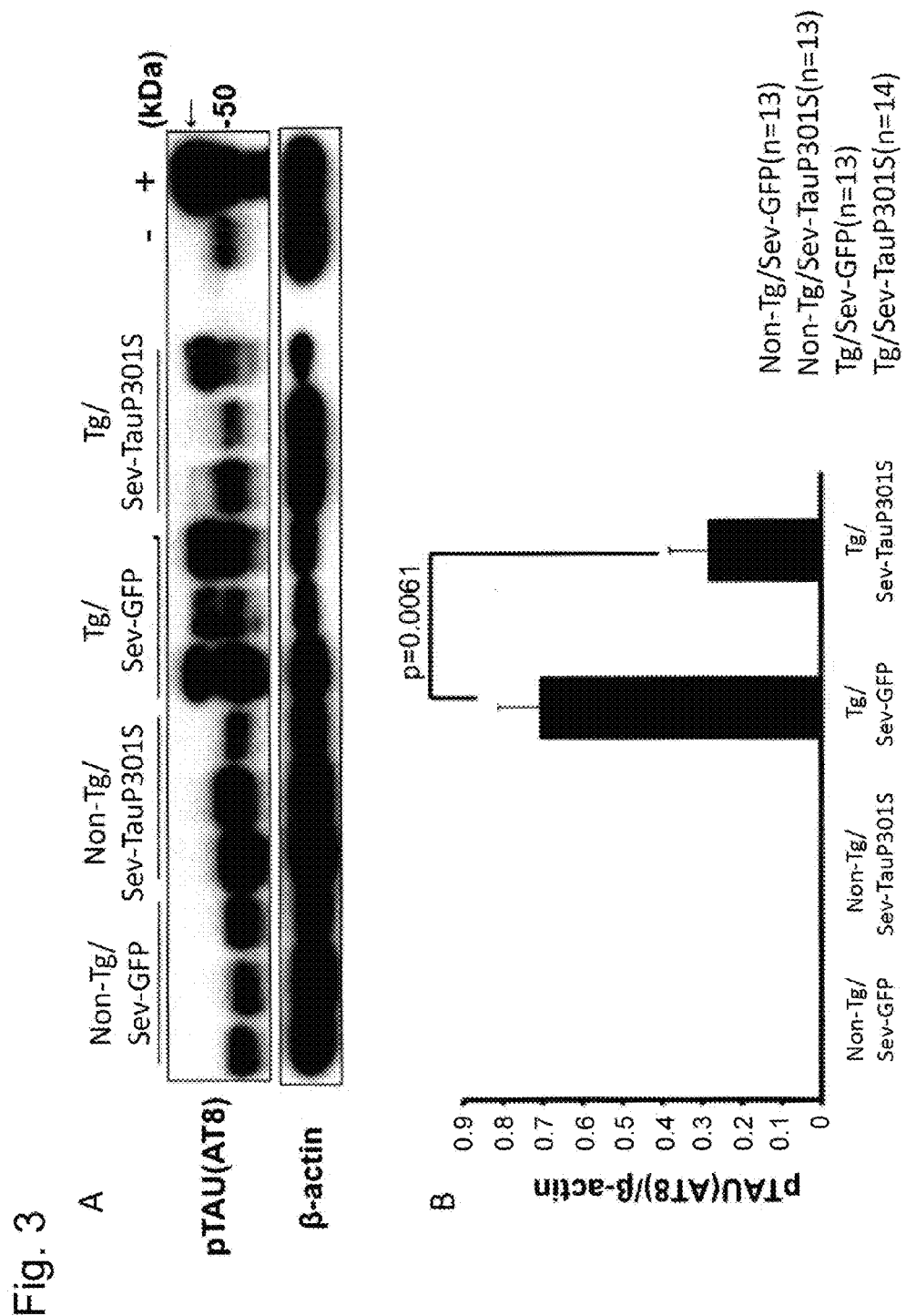
FIG. 3 describes the Sev-GFP-inoculated group. More specifically, (A) is a pair of photographs showing the results of nasally inoculating wild-type mice (Non-Tg) or tauopathy model mice (Tg) with Sev-TauP301S or Sev-GFP and evaluating the accumulation of phosphorylated tau protein (pTAU) in the whole hippocampus 5 months after inoculation by a western blott method. In addition, (B) is a graph showing the results of quantifying the amount of each protein by measuring the signal intensity of each band using an image analysis software (NIH Image, Ver. 1.63, NIH, US) and calculating the signal intensity ratio between each protein and β-actin as an internal control protein. The mean±standard error was calculated for each of the Sev-GFP-inoculated group and the Sev-TauP301S-inoculated group, and statistical analysis was performed by Student's t-test. The mouse groups and controls used in the test are as follows.

The amount of the accumulated phosphorylated tau protein was quantified by measuring the signal intensity of the band using an image analysis software (NIH Image, Ver. 1.63, NIH, US) to determine the signal intensity ratio thereof to β-actin as an internal control protein. The mean±standard error was determined for each of the control vaccine (Sev-GFP)-inoculated group and the tau vaccine (Sev-TauP301S)-inoculated group, and statistical analysis was performed by Student's t-test. As a result, the expression of phosphorylated tau protein in the hippocampus was shown to be suppressed in the Sev-TauP301S-inoculated group compared to the Sev-GFP-inoculated group (FIG. 3).

4) Induction of Antibody Reacting with Phosphorylated Tau in Hippocampus

The titer of the antibody in the serum reacting with tau in tissue was evaluated based on reactivity to the hippocampal tissue of tauopathy model mice to which Sev-TauP301S was not administered. The serum of each mouse to which ($5 \times 10^6$ CIU/animal of) Sev-TauP301S or Sev-GFP was administered was diluted 30 times, 100 times, 300 times, 1,000 times, and 3,000 times, reacted with the tissue section of the tauopathy model mouse hippocampus at 4° C. overnight, and then reacted with an Alexa546-labeled anti-mouse IgG antibody (Invitrogen) at room temperature for 1 hour for detection. The antibody titer of each mouse was evaluated by the maximum dilution at which reaction with the tissue was observed. The mean±standard error was determined for each of the Sev-GFP-inoculated group and the Sev-TauP301S-inoculated group, and statistical analysis was performed by Mann-Whitney U test.

As a result, reaction with the serum from the Sev-TauP301S-inoculated mouse resulted in the significantly high titer of the antibody reacting in the hippocampus compared to that with the serum from the mouse to which Sev-GFP was administered. The above results demonstrated that the antibody produced in the serum by the inoculation of Sev-TauP301S reacted with the hippocampus expressing phosphorylated tau (FIGS. 4a and 4c).

5) Activation of Microglia in Brain by Sev-TauP301S Inoculation

An experiment was performed for confirming a change in microglia, which are neuro-immunocompetent cells, in the brain by Sev-TauP301S inoculation.

Three-month old tauopathy model mice were each inoculated with Sev-TauP301S $5 \times 10^6$ CIU/animal; 5 months after inoculation, brain tissue was removed; the tissue section of the hippocampus was prepared; and immunostaining was carried out as follows.

An anti-Iba1 antibody (WAKO) was reacted with a mouse hippocampal coronal section at 4° C. overnight, and after washing, a combination of an Alexa488-labeled goat anti-rabbit IgG antibody (Invitrogen) as a secondary antibody and an Alexa546-labeled anti-mouse IgG antibody (Invitrogen) for detecting mouse IgG in tissue was reacted for 1 hour for detection by fluorescent double immunostaining. After immunostaining, the fluorescent image of the hippocampal CA3 region was taken using a multi-purpose microscope (BZ-9000, Keyence). As a result, a number of Iba1-positive cells were observed in the hippocampus in the Sev-TauP301S administration group compared to the Sev-GFP administration group as a control, and many of the positive cells were co-stained with the anti-mouse IgG antibody. Because Iba1 (Ionized calcium binding adapter molecule 1) increases in the expression level thereof as microglia are activated, Iba1 has been reported to be a molecule responsible for the activation of microglia (Ito D. et al., Brain Res. Mol. Brain Res. 57: 1-9, 1998), and further because mouse IgG probably recognizes TauP301S in tissue, the inoculation of Sev-TauP301S was thought to activate the reaction of microglia with TauP301S (FIG. 5).

For the increased activation of microglia by tau vaccine inoculation, there was suggested a possibility that 1) macrophages in the peripheral blood were activated by antigen presentation, collected in the brain by passing through the blood-brain barrier to become activated microglia, and phagocytized the mutant tau protein, or 2) the mutant tau protein passed through the blood-brain barrier, and microglia were activated by the direct presentation of the antigen in the brain and phagocytized the mutant tau protein.

6) ELISA Using Recombinant Phosphorylated Tau Protein as Antigen

To determine whether the antibody produced in the serum by Sev-TauP301S inoculation was an antibody specific to phosphorylated tau, ELISA was carried out using a recombinabt mutant tau protein (Sev-TauP301S) as an antigen.

The preparation of the recombinabt mutant tau protein was carried out based on a method of Sakaue et al. (Sakaue F. et al., J. Biol. Chem. 280: 31522-31529, 2005). Specifically, pRK172 vector incorporating TauP301S (1N4R type) was expressed in *Escherichia coli* (strain BL21-DE3), and the recombinant protein was purified from the bacterial cells by a phosphocellulose column (P11), 50% ammonium sulfate precipitation, heat treatment, and reverse-phase HPLC, lyophilized, and stored at 4° C.

The production of the anti-phosphorylated tau antibody in the serum was analyzed by the following ELISA method. The recombinant TauP301S protein (1 µg/ml/well) prepared by the above method was immobilized on a 96-well plate at 4° C. overnight.

The serum was collected from each inoculated mouse immediately before inoculation with Sev-TauP301S or Sev-GFP and on the 1st month after inoculation, used by diluting it 50 times, and placed in the plate at room temperature for 2 hours for reaction. After reaction, via washing, an HRP-labeled sheep anti-mouse IgG antibody (GE Healthcare) was reacted at room temperature for 1 hour. After reaction, the resultant was washed, color-developed using Opti-EIA TMB Substrate Reagent Set (BD), and quantified by measuring an absorbance at 450 nm. The serum of each mouse subcutaneously inoculated with the recombinant TAUP301S protein was used as a positive control serum and serially diluted, and absorbance was converted to units using the calibration curve between absorbance and units prepared defining an antibody titer in the neat serum as 1,000 units. An increase in the antibody titer was evaluated by the thus determined unit quantity after inoculating each mouse. As a result of the ELISA, it could be demonstrated that the inoculation of Sev-TauP301S resulted in the increased production of the anti-phosphorylated tau antibody in the serum (FIG. 6a).

The significant production of the tau-specific antibody in mice inoculated with the recombinant protein is probably due to a large amount of the mutant tau protein present in the blood in the early period of inoculation and a large number of antigen-presenting cells exposed to the mutant tau protein.

The amount of phosphorylated tau protein in the cerebrospinal fluid was also measured by the following method.

A 96-well plate is subjected to coating treatment with 3 μg/ml of an anti-phosphorylated antibody (AT8 antibody) at 4° C. overnight in advance. The cerebrospinal fluid (CSF) taken from each mouse inoculated with Sev-TauP301S or Sev-GFP was diluted 50 times and added to each well for reaction. As a positive control, the fluid obtained by homogenizing the brains of 14-month old tauopathy model mice was used by serially diluting it 100 to 102,400 times. An rabbit anti-human tau protein antibody, as a secondary antibody, and then a peroxidase-labeled sheep anti-rabbit IgG F(ab')$_2$ antibody were reacted, and the resultant was color-developed using a tetramethyl benzidone solution.

Absorbance at 450 nm was measured using an automated plate reader (Model 353; Thermo Scientific, Japan). As a result, phosphorylated tau protein was observed at a high concentration in the cerebrospinal fluid of tauopathy model mice (FIG. 6b).

7) Behavioral Analysis of Mouse

All behavioral experiments were carried out after being approved by Animal Research Committee, Graduate School of Medicine, Kyoto University (Kyoto, Japan). Tau vaccine was administered to the tauopathy model mice (P301 S Tau transgenic mice) used in the present experiments to evaluate its effect of improving behavioral abnormalities (reduced recent memory, unsociability, anxiety-like behavior, hyperactivity, activity amount, spatial learning, reference memory, sensory center, hearing, and the like) observed in dementia patients by the following methods.

(1) Social Interaction Test Under Novel Environment by Inoculation of Sev-TauP301S into Tauopathy Model Mouse The social interaction test is a test used for behavioral evaluation in a novel situation. Tauopathy model mice inoculated with Sev-TauP301S ($5 \times 10^6$ CIU/animal) or tauopathy model mice inoculated with Sev-GFP ($5 \times 10^6$ CIU/animal) were each placed in one box (40×40×30 cm) together with each of mice having not previously been present in the same cage thereas and allowed to explore freely for 10 minutes, on the 3rd month after inoculation. The social interaction was monitored through a CCD camera (Sony DXC-151A), and an image was scanned into a computer to automatically measure the number of contacts, the mean time per contact, and the distance of movement using Image SI software. As a result of analysis, the tauopathy model mice inoculated with Sev-TauP301S spent a long time in contacting the strange mice compared to the tauopathy model mice administered with Sev-GFP. From this analysis, the effect of improving the social interaction and the capability of response to the appearance of a novel mouse was observed (FIG. 7A).

(2) Social Interaction Test (Crawley Version) by Inoculation of Sev-TauP301S into Tauopathy Model Mice The Crawley's social interaction test is a test used for evaluating recent memory, formation of social relationship, and sociability with respect to different mice.

A device is partitioned into 3 spaces by panels, and small cages are set one on each corner of the spaces in both ends. A mouse having not previously been present in the same cage as a tauopathy model mouse is placed in a cage; Sev-TauP301S ($5 \times 10^6$ CIU/animal) or Sev-GFP ($5 \times 10^6$ CIU/animal) was then inoculated into the tauopathy model mouse; and the mouse on the 3rd month after inoculation was placed outside the cage and let alone for 10 minutes. After 10 minutes, a different mouse having not previously been present in the same cage as the tauopathy model mouse was placed in the other cage, and then near which of the mouse already present for 10 minutes (familiar side) and the new strange mouse (stranger side) the tauopathy model mouse inoculated with Sev-TauP301S or Sev-GFP stayed longer was examined by measuring the stay time to evaluate the social interaction.

As a result, Sev-GFP-inoculated tauopathy model mice had a longer stay time on the familiar side, while Sev-TauP301S-inoculated tauopathy model mice had a longer stay time on the stranger side, showing an effect of improving the social interaction and the recent memory in the different mice (FIG. 7B).

(3) Elevated Plus Maze Test by Inoculation of Sev-TauP301S into Tauopathy Model Mouse The elevated plus maze is a device for evaluating anxiety-like behavior and is composed of two open arms of the same size and two closed arms fitted with transparent walls (height, 15 cm)t. The closed arms are each fitted with transparent walls (height, 15 cm).

The arms and a central square portion are made of white plastic plates, and are positioned at a height of 50 cm from the floor. Tauopathy model mice inoculated with Sev-TauP301S ($5 \times 10^7$ CIU/animal, 3 times in total every 1 week) or tauopathy model mice inoculated with the same titer of Sev-GFP were each placed to face toward a closed arm in a square portion (5×5 cm) in the center of the maze and recorded for behavior for 10 minutes, 3 months after inoculation. The total number of entrances and exits in each of the four directions from the center of the maze (A), the percentage of the number of entrances and exits in the directions of the absence of fences (B), the total distance of movement of each mouse (C), and the percentage of the time staying in the fence-free place (D) were automatically measured using Image EP software. The tauopathy model mice inoculated with Sev-TauP301S had a significantly reduced time staying in the fence-free place, showing an effect of improving anxiety-like behavior and judgment for the risk of falling (FIG. 8D).

(4) Open Field Test by Inoculation of Recombinant Tau Protein into Tauopathy Model Mouse The open field test is a test for measuring the amount of activity and emotionality.

Tauopathy model mice were subcutaneously inoculated with 100 μg/animal per administration of recombinant tau protein (TAUP301S) 3 times in total every 2 weeks together with Adju-Phos adjuvant (Gentaur), and the open field test was carried out on the 1st month after inoculation. The inoculated mice were each placed in an open field test device (40 cm square) fitted with fences (height 30 cm; Accuscan Instruments) to evaluate free movement for 120 minutes by dividing the time into consecutive 5 minutes periods for the distance of movement of the inoculated mouse (A), the number of stretches (B), the time staying in the middle of the field (C), and stereotyped behavior (D). The tauopathy model mice inoculated with TAUP301S had a significantly reduced distance of movement, showing an effect of improving hyperactivity (restlessness) (FIG. 9A).

(5) Elevated Plus Maze Test by Inoculation of Recombinant Tau Protein into Tauopathy Model Mouse Tauopathy model mice were subcutaneously inoculated with 100 μg/animal per administration of recombinant tau protein (TAUP301S) 3 times in total every 2 weeks together with Adju-Phos adjuvant (Gentaur), and the analysis of the elevated plus maze was carried out on the 1st month after inoculation. The inoculated mice were each placed to face toward a closed arm in a square portion (5×5 cm) in the center of the maze and recorded for behavior for 10 minutes. The total number of entrances and exits in each of the four directions from the middle (A), the percentage of the number of entrances and exits in the directions of the absence of fences (B), the total distance of movement of each mouse (C), and the percentage of the time staying in the fence-free place (D) were automatically measured using Image EP software. The results obtained from tauopathy model mice inoculated with TAUP301S were not significantly different in the elevated plus maze analysis from those from control (adjuvant-administered) mice (FIG. 10).

(6) Open Field Test by Inoculation of DNA-Tau P301S into Tauopathy Model Mouse cDNA-Tau P301S (100 μg/animal per administration) was inoculated 6 times in total every week and then 3 times in total every two weeks 9 times in total into the left hind-limb thigh muscle of 5-month old tauopathy model mice at the time of start, and the open field test was carried out on the 1st month after inoculation. The inoculated mice were each placed in an open field test device (40 cm square) fitted with fences (height 30 cm; Accuscan Instruments) to evaluate free movement for 120 minutes by dividing the time into consecutive 5 minutes periods for the distance of movement of the inoculated mice (A), the number of stretches (B), the time staying on the middle of the field (C), and stereotyped behavior (D). The tauopathy model mice inoculated with cDNA-Tau P301S were demonstrated to have a reduced distance of movement, showing an effect of improving hyperactivity (restlessness) (FIG. 11A).

(7) Social Interaction Test Under Novel Environment by Inoculation of cDNA-Tau P301 S into Tauopathy Model Mouse cDNA-Tau P301S (100 μg/animal per administration) was inoculated 6 times in total every week and then 3 times in total every two weeks 9 times in total into the left hind-limb thigh muscle of 5-month old tauopathy model mice at the time of start, and these mice were each placed in one box (40×40×30 cm) together with each of mice having not previously been present in the same cage and allowed to explore freely for 10 minutes, on the 1st month after inoculation. The social interaction was monitored through a CCD camera (Sony DXC-151A), and an image was scanned into a computer to automatically measure the number of contacts, the mean time per contact, and the distance of movement using Image SI software. As a result analysis, the tauopathy model mice inoculated with cDNA-TauP 301S spent a significantly short time (p=0.0164, Student's t-test) in contacting the strange mice compared to tauopathy model mice inoculated with pcDNA3.1 (ATG-) (hereinafter referred to as cDNA-Empty) as a control (FIG. 12A). The tauopathy model mice inoculated with cDNA-Tau P301 S also had a short distance of movement compared to the tauopathy model mice inoculated with cDNA-Empty. (FIG. 12B). As a result, the inoculation of cDNA-Tau P301S was observed to improve hyperactivity as in the open field test.

(8) Barnes Maze Test by Inoculation of Sev-TauP301S into Tauopathy Model Mouse

The Barnes maze test is a test for examining spatial learning and reference memory. One circular plate is provided with 12 holes, under only one of which a dark box is placed. Sev-TauP301S ($5\times10^6$ CIU/animal) or Sev-GFP ($5\times10^6$ CIU/animal) was inoculated into tauopathy model mice and wild-type mice, and the test was carried out on 4th month after inoculation. First, mice were trained for a certain period of time to remember the spatial location of the dark box (training period), and after a lapse of 24 hours after the end of training, spatial learning and reference memory were evaluated by the time staying around the targeted hole (under which the dark box had been placed) (probe test). In tauopathy model mice, the inoculation of Sev-TauP301S reduced the time until arrival at the target (FIG. 15B) and further increased the time staying around the hole as the target (FIG. 15C), confirming an improvement effect.

(9) Conditioned Fear Test by Inoculation of Sev-TauP301S into Tauopathy Model Mouse The conditioned fear test is a test for measuring contextual learning and attention ability. Sev-TauP301S ($5\times10^6$ CIU/animal) or Sev-GFP ($5\times10^6$ CIU/animal) was inoculated into tauopathy model mice and wild-type mice, and the test was carried out on 4th month after inoculation. The phenomenon of freezing may occur by applying electroshock to a mouse placed in a box, giving another stimulus (for example, sound) to the mouse in the same box in which it experienced the electroshock, and after a lapse of a certain time, placing the mouse in the same box or placing the mouse in another box before stimulation by the same sound. The contextual learning and the attention ability were evaluated by the occurrence ratio of the freezing. In tauopathy model mice, the inoculation of Sev-TauP301S reduced the occurrence ratio of the freezing, showing an improvement effect (FIG. 16C).

(10) Body Measurement after Inoculation of Sev-TauP301S into Tauopathy Model Mouse Sev-TauP301S ($5\times10^6$ CIU/animal) or Sev-GFP ($5\times10^6$ CIU/animal) was inoculated into tauopathy model mice and wild-type mice, and body weight, body temperature, grip strength, and wire hang time were measured on the 1st month after inoculation. The results are shown in FIG. 17. No significant difference was observed between the groups.

(11) Social Interaction Measurement Test by Inoculation of Sev-TauP301S into Tauopathy Model Mouse The social interaction measurement test is a test for measuring social interaction by placing 2 mice to be tested in a box and measuring the number of contacts, the duration of contact, the distance of movement of the mice, and the like for 10 minutes. Sev-TauP301S ($5\times10^6$ CIU/animal) or Sev-GFP ($5\times10^6$ CIU/animal) was inoculated into tauopathy model mice and wild-type mice, and the test was carried out on 2nd month after inoculation. As a result, in tauopathy model mice inoculated with Sev-TauP301S, the number of contacts was increased (FIG. 18B), the duration of active contact was prolonged (FIG. 18C), and the total movement distance was increased (FIG. 18E), showing an improvement effect.

(12) Prepulse Inhibition Test by Inoculation of Sev-TauP301S into Tauopathy Model Mouse The prepulse inhibition test is a test for evaluating the sensory center, hearing, the response of jumping up (to a stimulus), and the like. Tauopathy model mice and wild-type mice inoculated with Sev-TauP301S ($5\times10^6$ CIU/animal) or tauopathy model mice and wild-type mice inoculated with Sev-GFP (5×10$^6$ CIU/animal) were subjected to the prepulse inhibition test on the 3rd month after inoculation.

As a result, no freezing-suppressing effect by the inoculation of Sev-TauP301S was observed, and no significant difference was noted between the groups (FIG. 19).

(13) Open Field Test by Inoculation of Sev-TauP301S into Tauopathy Model Mouse

Sev-TauP301S (5×10$^6$ CIU/animal) or Sev-GFP (5×10$^6$ CIU/animal) was inoculated into tauopathy model mice and wild-type mice, and the open field test was carried out on 1st month after inoculation. (A) shows the total distance of movement; (B), the amount of activity in the vertical direction; (C), the time staying in a central part; and (D), the number of stereotyped behaviors.

No significant difference was observed between the groups (FIG. 20).

(14) Open Field Test in Tauopathy Model Mouse and Wild-Type Mouse

The open field test was carried out in wild-type mice and tauopathy model mice. (A) shows the total distance of movement; (B), the amount of activity in the vertical direction; (C), the time staying in a central part; and (D), the number of stereotyped behaviors.

The tauopathy model mice had a long total distance of movement (A), a high amount of activity in the vertical direction (B), and a long time staying in the central part (C), when compared to the wild-type mice. No significant difference was observed in the number of stereotyped behaviors (D) (FIG. 21).

(15) Elevated Plus Maze Test in Tauopathy Model Mouse and Wild-Type Mouse

The elevated plus maze test was carried out in tauopathy model mice and wild-type mice.

As a result, the percentage of entries into the fence-free open arms (B) and the time staying on the fence-free open arms showed significantly high values in the tauopathy model mice compared to those in the wild-type mice (FIG. 22).

(16) Prepulse Inhibition Test in Tauopathy Model Mouse and Wild-Type Mouse

The prepulse inhibition test was carried out in tauopathy model mice and wild-type mice. Compared to the wild-type mice, the tauopathy model mice showed a low startle response to a sound (FIG. 23A) but had a high value in the percentage of inhibition of a startle response, when a small sound and then a large sound were emitted (FIG. 23B).

(17) Expression of Tau Protein in Brain Tissue of Tauopathy Model Mouse and Wild-Type Mouse The expression levels of tau protein in the brain tissue of tauopathy model mice and wild-type mice were histopathologically compared.

No aggregation image or inclusion of tau was seen, but phosphorylated protein was prominently observed in the brain tissue of the tauopathy model mice compared to in that of the wild-type mice (FIG. 24). It is considered that the cingulate cortex, cortical amygdaloid nucleus, hippocampus, and the like in which phosphorylated tau was abundantly observed are associated with anxiety disorder, and such hippocampus is associated with impaired memory, thus suggesting that the accumulation of phosphorylated tau in these tissues resulted in behavioral abnormalities.

(18) Body Measurement in Tauopathy Model Mouse and Wild-Type Mouse

General body measurement was carried out in 13-week old tauopathy model and wild-type mice.

(A) shows body weight; (B), rectal temperature; (C), grip strength; and (D), the results of a wire hang test.

No significant difference was observed between the tauopathy model mice and the wild-type mice (FIG. 25).

(19) Social Interaction Test in Tauopathy Model Mouse and Wild-Type Mouse (Novel Setting)

The social interaction test was carried out in tauopathy model mice or wild-type mice.

As a result of the social interaction test, no significant difference was observed between the tauopathy model mice and the wild-type mice (FIG. 26).

(20) Conditioned Fear Test in Tauopathy Model Mouse and Wild-Type Mouse

The conditioned fear test was carried out in wild-type mice and tauopathy model mice. The occurrence ratio of freezing showed low values in tauopathy model mice compared to in wild-type mice; however, overall, no great significant difference was observed (FIG. 27).

(21) Barnes Maze Test in Tauopathy Model Mouse and Wild-Type Mouse

The Barnes maze test was carried out in wild-type mice and tauopathy model mice. FIGS. 28 (A) to (C) shows the results obtained during the period of training. FIG. 28 (D) shows the results of a probe test after a lapse of 24 hours after training.

During the period of training, no significant difference was observed between the tauopathy model mice and the wild-type mice (FIGS. 28A to C).

For the probe test, the times staying around a hole next to the target and around the hole as the target were short in the tauopathy model mice compared to in the wild-type mice (FIG. 28D).

(22) Expression of Tau Protein in Brain Tissue of Tauopathy Model Mouse and Wild-Type Mouse The expression levels of tau protein in the brain tissues of tauopathy model mice and wild-type mice were histopathologically compared.

No aggregation image or inclusion of tau protein was seen, but phosphorylated protein was prominently observed in the brain tissue of the tauopathy model mice compared to in that of the wild-type mice (FIG. 24). It is considered that the cingulate cortex, cortical amygdaloid nucleus, hippocampus, and the like in which phosphorylated tau is abundantly observed are associated with anxiety disorder, and such hippocampus is associated with impaired memory, thus suggesting that the accumulation of phosphorylated tau in these tissues resulted in behavioral abnormalities.

INDUSTRIAL APPLICABILITY

The vaccine of the present invention is medically useful because it is effective in improving the symptoms of diseases caused by the abnormal accumulation of tau protein in the central nervous system (tauopathy), especially tautopathy dementia.

SEQUENCE LISTING FREE TEXT

SEQ ID NOS: 4 to 11: primer
SEQ ID NOS: 12, 13: artificial DNA

All publications, patents, and patent applications cited in this application are intended to be incorporated herein by reference in their entirety.

The invention claimed is:

1. A vaccine for treating tauopathy dementia, comprising an adeno-associated virus vector as an active ingredient,
   wherein the vector comprises a nucleic acid encoding a full length mutant tau protein linked to a secretory signal sequence,
   wherein the full length mutant tau protein comprises a substitution mutation of an amino acid residue, P301S, at a position 301 of the amino acid sequence of SEQ ID NO: 1 of a tau protein, and
   wherein the vector is capable of inducing an antibody to the full length mutant tau protein in a subject in a sustained manner and the antibody being capable of reacting with phosphorylated tau protein present in the hippocampus of the subject.

2. The vaccine according to claim 1, wherein the secretory signal sequence is a signal sequence of amyloid precursor protein or a signal sequence of CD59.

3. The vaccine according to claim 1, wherein the vaccine has an effect of improving at least one symptom of abnormal social interaction, abnormal anxiety-like behavior, and impaired memory in a subject.

4. The vaccine according to claim 1, wherein the vaccine has an effect of activating microglia in the brain of a subject and thereby suppressing the accumulation of the mutant tau protein.

5. The vaccine according to claim 1, wherein the vector is capable of inducing an antibody to phosphorylated mutant tau protein.

* * * * *

SEQUENCE LISTING

<160> NUMBER OF SEQ ID NOS: 13

<210> SEQ ID NO 1
<211> LENGTH: 441
<212> TYPE: PRT
<213> ORGANISM: Homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365
```

| Lys | Lys | Ile | Glu | Thr | His | Lys | Leu | Thr | Phe | Arg | Glu | Asn | Ala | Lys | Ala |
|---|---|---|---|---|---|---|---|---|---|---|---|---|---|---|---|
| | 370 | | | | 375 | | | | | 380 | | | | | |

| Lys | Thr | Asp | His | Gly | Ala | Glu | Ile | Val | Tyr | Lys | Ser | Pro | Val | Val | Ser |
|---|---|---|---|---|---|---|---|---|---|---|---|---|---|---|---|
| 385 | | | | | 390 | | | | | 395 | | | | | 400 |

| Gly | Asp | Thr | Ser | Pro | Arg | His | Leu | Ser | Asn | Val | Ser | Ser | Thr | Gly | Ser |
|---|---|---|---|---|---|---|---|---|---|---|---|---|---|---|---|
| | | | | 405 | | | | | 410 | | | | | 415 | |

| Ile | Asp | Met | Val | Asp | Ser | Pro | Gln | Leu | Ala | Thr | Leu | Ala | Asp | Glu | Val |
|---|---|---|---|---|---|---|---|---|---|---|---|---|---|---|---|
| | | | 420 | | | | | 425 | | | | | 430 | | |

| Ser | Ala | Ser | Leu | Ala | Lys | Gln | Gly | Leu |
|---|---|---|---|---|---|---|---|---|
| | | 435 | | | | | 440 | |

```
<210> SEQ ID NO 2
<211> LENGTH: 62
<212> TYPE: DNA
<213> ORGANISM: Homo sapiens

<400> SEQUENCE: 2
ggtctagaat gctgcccggt ttggcactgc tcctgctggc cgcctggacg gctcgggcgc    60
tt                                                                  62

<210> SEQ ID NO 3
<211> LENGTH: 75
<212> TYPE: DNA
<213> ORGANISM: Homo sapiens

<400> SEQUENCE: 3
atgggaatcc aaggagggtc tgtcctgttc gggctgctgc tcgtcctggc tgtcttctgc    60
cattcaggtc atagc                                                    75

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
gctgagcccc gccaggag                                                 18

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
tcacaaaccc tgcttggcca g                                             21

<210> SEQ ID NO 6
<211> LENGTH: 41
<212> TYPE: DNA
<213> ORGANISM: Artificial
<220> FEATURE:
<223> OTHER INFORMATION: primer

<400> SEQUENCE: 6
aaagaattcg gcttggtcta gaatgctgcc cggtttggca c                        41

<210> SEQ ID NO 7
<211> LENGTH: 30
<212> TYPE: DNA
```

```
<213> ORGANISM: Artificial
<220> FEATURE:
<223> OTHER INFORMATION: primer

<400> SEQUENCE: 7
aaagaattct cacaaaccct gcttggccag                                    30

<210> SEQ ID NO 8
<211> LENGTH: 18
<212> TYPE: DNA
<213> ORGANISM: Artificial
<220> FEATURE:
<223> OTHER INFORMATION: primer

<400> SEQUENCE: 8
gctgagcccc gccaggag                                                 18

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
tcacaaaccc tgcttggcca g                                             21

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
ttgaattcgc caccatggga atccaaggag                                    30

<210> SEQ ID NO 11
<211> LENGTH: 28
<212> TYPE: DNA
<213> ORGANISM: Artificial
<220> FEATURE:
<223> OTHER INFORMATION: primer

<400> SEQUENCE: 11
aattctcgag tcacaaaccc tgcttggc                                      28

<210> SEQ ID NO 12
<211> LENGTH: 1323
<212> TYPE: DNA
<213> ORGANISM: Artificial
<220> FEATURE:
<223> OTHER INFORMATION: synthetic DNA
<220> FEATURE:
<221> NAME/KEY: CD59 signal sequence
<222> LOCATION: (13)..(87)

<400> SEQUENCE: 12
gaattcgcca ccatgggaat ccaaggaggg tctgtcctgt tcgggctgct gctcgtcctg    60
gctgtcttct gccattcagg tcatagcgct gagccccgcc aggagttcga agtgatggaa   120
gatcacgctg ggacgtacgg gttggggac aggaaagatc agggggggcta caccatgcac   180 caagaccaag agggtgacac ggacgctggc ctgaaagaat ctcccctgca gaccccacct   240
gaggacggat ctgaggaacc gggctctgaa acctctgatg ctaagagcac tccaacagcg   300
```

```
gaagctgaag aagcaggcat tggagacacc cccagcctgg aagacgaagc tgctggtcac    360
gtgacccaag ctcgcatggt cagtaaaagc aaagacggga ctggaagcga tgacaaaaaa    420
gccaagggggg ctgatggtaa acgaagatc gccacaccgc ggggagcagc ccctccaggc    480
cagaagggcc aggccaacgc caccaggatt ccagcaaaaa cccgcccgc tccaaagaca     540
ccacccagct ctggtgaacc tccaaaatca ggggatcgca gcggctacag cagccccggc    600
tccccaggca ctcccggcag ccgctcccgc accccgtccc ttccaacccc acccacccgg    660
gagcccaaga aggtggcagt ggtccgtact ccacccaagt cgccgtcttc cgccaagagc    720
cgcctgcaga cagcccccgt gcccatgcca gacctgaaga atgtcaagtc caagatcggc    780
tccactgaga acctgaagca ccagccggga ggcgggaagg tgcagataat taataagaag    840
ctggatctta gcaacgtcca gtccaagtgt ggctcaaagg ataatatcaa acacgtcagt    900
ggaggcggca gtgtgcaaat agtctacaaa ccagttgacc tgagcaaggt gacctccaag    960
tgtggctcat taggcaacat ccatcataaa ccaggaggtg gccaggtgga agtaaaatct   1020
gagaagcttg acttcaagga cagagtccag tcgaagattg gtccctgga  caatatcacc   1080
cacgtccctg gcggaggaaa taaaaagatt gaaacccaca gctgaccttc cgcgagaac    1140
gccaaagcca gacagacca  cggggcgag  atcgtgtaca agtcgccagt ggtgtctggg   1200
gacacgtctc cacggcatct cagcaatgtc tcctccaccg gcagcatcga catggtagac   1260
tcgccccagc tcgccacgct agctgacgag gtgtctgcct ccctggccaa gcaggggtttg  1320
tga                                                                  1323
```

<210> SEQ ID NO 13
<211> LENGTH: 1315
<212> TYPE: DNA
<213> ORGANISM: Artificial
<220> FEATURE:
<223> OTHER INFORMATION: synthetic DNA
<220> FEATURE:
<221> NAME/KEY: APP signal sequence
<222> LOCATION: (20)..(73)

<400> SEQUENCE: 13

```
gaattcggct tggtctagaa tgctgcccgg tttggcactg ctcctgctgg ccgcctggac    60
ggctcgggcg cttgctgagc cccgccagga gttcgaagtg atggaagatc acgctgggac   120
gtacgggttg ggggacagga agatcagggg ggctacacc  atgcaccaag accaagaggg   180
tgacacggac gctggcctga agaatctcc  cctgcagacc ccactgagg  acggatctga   240
ggaaccgggc tctgaaacct ctgatgctaa gagcactcca acagcggaag ctgaagaagc   300
aggcattgga gacacccccca gcctggaaga cgaagctgct ggtcacgtga cccaagctcg   360
catggtcagt aaaagcaaag acgggactgg aagcgatgac aaaaaagcca ggggggctga   420
tggtaaaacg aagatcgcca caccgcgggg agcagcccct ccaggccaga agggccaggc   480
caacgccacc aggattccag caaaaacccc gccggctcca agacaccac  ccagctctgg   540
tgaacctcca aaatcagggg atcgcagcgg ctacagcagc ccggctccc  caggcactcc   600
cggcagccgc tccgcaccc  cgtcccttcc aaccccaccc acccgggagc caagaaggt   660
ggcagtggtc cgtactccac ccaagtcgcc gtcttccgcc aagagccgcc tgcagacagc   720
ccccgtgccc atgccagacc tgaagaatgt caagtccaag atcggctcca ctgagaacct   780
gaagcaccag ccgggaggcg ggaaggtgca gataattaat aagaagctgg atcttagcaa   840
cgtccagtcc aagtgtggct caaaggataa tatcaaacac gtctcgggag gcggcagtgt   900
```

-continued

| | | | | | |
|---|---|---|---|---|---|
| gcaaatagtc | tacaaaccag | ttgacctgag | caaggtgacc | tccaagtgtg | gctcattagg | 960
| caacatccat | cataaaccag | gaggtggcca | ggtggaagta | aaatctgaga | agcttgactt | 1020
| caaggacaga | gtccagtcga | agattgggtc | cctggacaat | atcacccacg | tccctggcgg | 1080
| aggaaataaa | aagattgaaa | cccacaagct | gaccttccgc | gagaacgcca | aagccaagac | 1140
| agaccacggg | gcggagatcg | tgtacaagtc | gccagtggtg | tctggggaca | cgtctccacg | 1200
| gcatctcagc | aatgtctcct | ccaccggcag | catcgacatg | gtagactcgc | cccagctcgc | 1260
| cacgctagct | gacgaggtgt | ctgcctccct | ggccaagcag | ggtttgtgag | aattc | 1315